US012753210B2

(12) United States Patent
Lovley et al.

(10) Patent No.: US 12,753,210 B2
(45) Date of Patent: Oct. 6, 2026

(54) **EXPRESSION OF ELECTRICALLY CONDUCTIVE PROTEIN NANOWIRES IN *ESCHERICHIA COLI***

(71) Applicant: University of Massachusetts, Boston, MA (US)

(72) Inventors: Derek R. Lovley, Amherst, MA (US); Toshiyuki Ueki, Amherst, MA (US); David Walker, Boston, MA (US); Trevor Woodard, Shelburne, MA (US); Kelly Nevin Lovley, Amherst, MA (US)

(73) Assignee: University of Massachusetts, Westborough, MA (US)

( * ) Notice: Subject to any disclaimer, the term of this patent is extended or adjusted under 35 U.S.C. 154(b) by 1147 days.

(21) Appl. No.: 17/778,769

(22) PCT Filed: Nov. 20, 2020

(86) PCT No.: PCT/US2020/061609
§ 371 (c)(1),
(2) Date: May 20, 2022

(87) PCT Pub. No.: WO2021/102327
PCT Pub. Date: May 27, 2021

(65) Prior Publication Data
US 2023/0040959 A1 Feb. 9, 2023

Related U.S. Application Data

(60) Provisional application No. 62/938,913, filed on Nov. 21, 2019.

(51) Int. Cl.
*C07K 14/245* (2006.01)
*C12N 15/52* (2006.01)
*C12N 15/72* (2006.01)

(52) U.S. Cl.
CPC ............ *C07K 14/245* (2013.01); *C12N 15/52* (2013.01); *C12N 15/72* (2013.01)

(58) Field of Classification Search
CPC .... C07K 14/245; C07K 14/195; C12N 15/52; C12N 15/72; C12N 15/70; C08H 1/00; C08L 89/00
See application file for complete search history.

(56) References Cited

U.S. PATENT DOCUMENTS 7,498,155 B2 3/2009 Lovley et al.
8,232,584 B2 7/2012 Lieber et al.
8,608,921 B2 12/2013 Li et al.
8,729,233 B2 5/2014 Reguera et al.
8,846,890 B2 9/2014 Reguera et al.
9,102,521 B2 8/2015 Lieber et al.
9,234,508 B2 1/2016 Sahin
9,601,227 B2 3/2017 Reguera et al.
9,694,344 B2 7/2017 Song et al.
9,697,460 B2 7/2017 Collins et al.
9,784,249 B2 10/2017 LI et al.
10,083,974 B1 9/2018 Huang et al.
10,311,357 B2 6/2019 Nugent et al.
10,388,370 B2 8/2019 Schmidt et al.
10,640,954 B2 5/2020 Kim et al.
10,684,244 B2 6/2020 Chen
10,741,778 B2 8/2020 Kirsch et al.
11,043,265 B2 6/2021 Li et al.
11,063,227 B2 7/2021 Kirsch et al.
11,066,449 B2 7/2021 Lovley et al.
11,133,058 B1 9/2021 Philip et al.
11,631,824 B2 4/2023 Yao et al.
11,823,808 B2 11/2023 Lovley et al.
11,982,637 B2 5/2024 Yao et al.
12,215,374 B2 2/2025 Dastoor
12,264,207 B2 4/2025 Chen et al.
12,320,802 B2 6/2025 Lovley et al.
12,451,821 B2 10/2025 Yao et al.
12,549,114 B2 2/2026 Yao et al.
2006/0057051 A1 3/2006 Dai et al.
2006/0113880 A1 6/2006 Pei et al.
2007/0157967 A1 7/2007 Mershin et al.
2008/0283799 A1 11/2008 Alden et al.
2009/0188784 A1 7/2009 Lee et al.
2010/0119879 A1 5/2010 Girguis et al.
(Continued)

FOREIGN PATENT DOCUMENTS

CN 1527051 A 9/2004
CN 108365776 A 8/2018
(Continued)

OTHER PUBLICATIONS

Pratt et al. Genetic analysis of *Escherichia coli* biofilm formation: roles of flagella, motility, chemotaxis and type I pili., Molecular Microbiology (1998), 30(2): 285-293). (Year: 1998).*
Whisstock et al. Quaterly Reviews of Biophysics, 2003, "Prediction of protein function from protein sequence and structure", 36(3): 307-340. (Year: 2003).*
Kisselev L., Polypeptide release factors in prokaryotes and eukaryotes: same function, different structure. Structure, 2002, vol. 10: 8-9. (Year: 2002).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
(Continued)

*Primary Examiner* — Iqbal H Chowdhury
(74) *Attorney, Agent, or Firm* — Hamilton, Brook, Smith & Reynolds, P.C.

(57) ABSTRACT

The present invention provides, in various embodiments, genetically modified aerobic bacteria, polynucleotides and methods for expressing and/or harvesting electrically conductive protein nanowires (e-PNs). The present invention also provides e-PNs produced using the genetically modified aerobic bacteria, polynucleotides and methods.

16 Claims, 10 Drawing Sheets

Specification includes a Sequence Listing.

(56) References Cited

U.S. PATENT DOCUMENTS

| | | | |
|---|---|---|---|
| 2014/0330337 | A1 | 11/2014 | Linke et al. |
| 2014/0336357 | A1 | 11/2014 | Reguera et al. |
| 2018/0007819 | A1 | 1/2018 | Vajo et al. |
| 2018/0195997 | A1 | 7/2018 | Li et al. |
| 2018/0202964 | A1 | 7/2018 | Alam et al. |
| 2018/0371029 | A1 | 12/2018 | Lovley et al. |
| 2019/0148085 | A1 | 5/2019 | Kim et al. |
| 2020/0090830 | A1 | 3/2020 | Lovley et al. |
| 2021/0002332 | A1 | 1/2021 | Malvankar et al. |
| 2021/0070811 | A1 | 3/2021 | Reguera et al. |
| 2021/0336169 | A1 | 10/2021 | Yao et al. |
| 2021/0341406 | A1 | 11/2021 | Yao et al. |
| 2021/0344286 | A1 | 11/2021 | Yao et al. |
| 2023/0160885 | A1 | 5/2023 | Lovley et al. |
| 2023/0344369 | A1 | 10/2023 | Jun et al. |
| 2025/0379528 | A1 | 12/2025 | Yao et al. |

FOREIGN PATENT DOCUMENTS

| | | | |
|---|---|---|---|
| KR | 10-1203181 | B1 | 11/2012 |
| WO | 2013/033456 | A1 | 3/2013 |
| WO | 2017/015306 | A2 | 1/2017 |
| WO | 2019/144931 | A1 | 8/2019 |
| WO | 2019/169331 | A1 | 9/2019 |
| WO | 2020/069523 | A1 | 4/2020 |
| WO | 2020/191281 | A1 | 9/2020 |
| WO | 2021/102327 | A1 | 5/2021 |

OTHER PUBLICATIONS

Guterman, T. and Gazit, E., “Toward peptide-based bioelectronics: reductionist design of conductive pili mimetics,” Bioelectron Med (Lond.), vol. 1; No. 2; 131-137 (2018).

Liu, X. et al., “Biological synthesis of high-conductive pili in aerobic bacterium Pseudomonas aeruginosa,” Applied Microbiology and Biotechnology, vol. 103; 1535-1544 (2019).

Reardon, P.N. and Mueller, K.T., “Structure of the Type IVa Major Pilin from the Electrically Conductive Bacterial Nanowires of Geobacter sulfurreducens,” The Journal of Biological Chemistry, vol. 288; No. 41; 29250-29256 (2013).

Rico, A.L. et al., “Functional reconstitution of the type IVa pilus assembly system from enterohaemorrhagic *Escherichia coli*,” Mol. Microbiol., vol. 111; No. 3; 732-749 (2019).

Notification of Transmittal of The International Search Report and The Written Opinion for International Application No. PCT/US2020/061609, entitled: “Expression of Electrically Conductive Protein Nanowires in *Escherichia Coli*,” mailed Mar. 15, 2021.

Ueki et al., “Genetic switches and related tools for controlling gene expression and electrical outputs of Geobacter sulfurreducens”, J Ind Microbiol Biotechnol, vol. 43, 2016, pp. 1561-1575.

Walker et al., “Syntrophus Conductive Pili Demonstrate that Common Hydrogen-Donating Syntrophs can have a Direct Electron Transfer Option”, The ISME Journal, vol. 14, 2020, pp. 1-19.

Walker et al., “The Archaellum of Methanospirillum hungatei is Electrically Conductive”, ASM Journals, vol. 10, No. 2, 2019, 11 Pages.

Wals et al., “Unnatural amino acid incorporation in *E. coli*: current and future applications in the design of therapeutic proteins”, Frontiers in Chemistry, vol. 2, Apr. 2014, pp. 1-12.

Notice of Allowance for U.S. Appl. No. 18/306,860, mailed Oct. 9, 2025.

Pontrelli et al., “*Escherichia coli* as a host for metabolic engineering”, Metabolic Engineering, 2018, pp. 1-31.

Schleif, “AraC protein: a love-hate relationship”, BioEssays 25.3, vol. 25, 2003, pp. 274-282.

Shen, et al., “Moisture-enabled electricity generation: from physics and materials to self-powered applications,” Adv. Mater. 32, 2003722 (2020).

Smolskaya et al., “Site-Specific Incorporation of Unnatural Amino Acids into *Escherichia coli* Recombinant Protein: Methodology Development and Recent Achievement”, Biomolecules, vol. 9, Jun. 28, 2019, pp. 1-17.

Sun et al., “Conductive Composite Materials Fabricated from Microbially Produced Protein Nanowires”, Small, 2018, pp. 1-5.

Tan et al., “The low conductivity of geobacter uraniireducens pili suggests a diversity of extracellular electron transfer mechanisms in the genus geobacter”, Frontiers in Microbiology, vol. 7, Jun. 2016, pp. 1-10.

Baba et al., “Construction of *Escherichia coli* K-12 in-frame, single-gene knockout mutants: the Keio collection”, Molecular Systems Biology, vol. 2, 2006, pp. 1-11.

Chang et al., “Architecture of the type IVa pilus machine”, Biophysical Journal, 2016, pp. 1-18.

Choi et al., “Systems Metabolic Engineering of *Escherichia coli*”, ASMScience.org/EcoSalPlus, 2016, pp. 1-56.

Creasey et al., “Improved Electrical Conductance through Self-Assembly of Bioinspired Peptides into Nanoscale Fibers”, Materials Chemistry and Physics, vol. 158, May 5, 2015, 26 pages.

Creasey et al., Microbial nanowires—Electron transport and the role of synthetic analogues, Acta Biomaterialia, Mar. 2018, pp. 1-30, vol. 69.

Cuthbertson et al., “The TetR Family of Regulators”, Microbiology and Molecular Biology Reviews, vol. 77, No. 3, Sep. 2013, pp. 440-475.

Datsenko et al., “One-step inactivation of chromosomal genes in *Escherichia coli* K-12 using PCR products”, PNAS, vol. 97, No. 12, Jun. 6, 2000, pp. 6640-6645.

De Boer et al., “The tac promoter: A functional hybrid derived from the trp and lac promoters”, Proc. Natl. Acad. Sci. USA, vol. 80, pp. 21-25, Jan. 1983.

Hanahan, “Studies on transformation of *Escherichia coli* with plasmids”, Journal of Molecular Biology, 1983, pp. 557-580, No. 166(4).

Hospenthal et al., “A comprehensive guide to pilus biogenesis in Gram-negative bacteria”, Nature Reviews, Microbiology, vol. 15, Jun. 2017, pp. 365-379.

Ing et al., “Going the Distance: Long-Range Conductivity in Protein and Peptide Bioelectronic Materials”, The Journal of Physical Chemistry B, vol. 122, No. 46, Sep. 21, 2018, 22 Pages.

Ing et al., Electronic Conductivity in Biomimetic a-Helical Peptide Nanofibers and Gels, Mar. 14, 2018, ACS Nano, pp. 2652-2661, vol. 12.

Liu et al., Power generation from ambient humidity using protein nanowires, Feb. 17, 2020, Nature, 550-554, 578.

Zhao; F. et al., “Direct power generation from a graphene oxide film under moisture,” Adv. Mater. 27, 4351-4357 (2015).

Zhou, et al., “Origin of the chemical and kinetic stability of graphene oxide,” Sci. Rep. 3, 2484 (2013).

Zhou, Jiangfeng, et al, “Development of nanowire-modified electrodes applied in the locally enhanced electric field treatment (LEE FT) for water disinfection”, 2020, Journals of Materials Chemistry. Article, 12262-12277 (Year: 2020).

Malvankar et al., “Microbial nanowires for bioenergy applications”, Current Opinion in Biotechnology, vol. 27, 2017, pp. 88-95.

Malvankar et al., “Microbial Nanowires: A New Paradigm for Biological Electron Transfer and Bioelectronics”, ChemSusChem Concepts, vol. 5, 2012, pp. 1039-1046.

Malvankar et al., “Visualization of charge propagation along individual pili proteins using ambient electrostatic force microscopy” Nature Nanotechnology, vol. 9, Dec. 2014, pp. 1-10.

Marquez, A et al., “Nanoporous silk films with capillary action and size-exclusion capacity for sensitive glucose determination in whole blood,” Lab Chip 21, 608-615 (2021).

Miaudet et al, “Thermo-electrical properties of PVA-nanotube composite fibers,” Elsevier, ScienceDirect, Polymer 48 (2007) 4068-4074.

Milano, Gianluca, et al, “Self-limited single nanowire systems combining all-in—0ne memristive and neuromorphic functionalities”, Dec. 2018, Nature Communications, Article No. 5151. pp. 1-10 (Year. 2018).

Milano, Gianluca, et al, “Self-limited single nanowire systems combining all-in—One memristive and neuromorphic functionalities”, Dec. 2018, Nature Communications, Article No. 5151. pp. 1-10 (Year: 2018).

(56) References Cited

OTHER PUBLICATIONS

Nevin et al., "Anode Biofilm Transcriptomics Reveals Outer Surface Components Essential for High Density Current Production in Geobacter sulfurreducens Fuel Cells", PLoS ONE, vol. 4, Issue 5, May 2009, pp. 1-11.
Nevin et al., "Power output and columbic efficiencies from biofilms of Geobacter sulfurreducens comparable to mixed community microbial fuel cells", Environmental Microbiology, vol. 10, No. 10, 2008, pp. 2505-2514.
Ogura et al.,"A Conductive and Humidity-Sensitive Composite Film Derived from Poly(o-phenylenediamine) and Polyvinyl Alcohol," J. Electrochem. Soc., vol. 142, No. 9, Sep. 1995.
Pang, et al, "The pressure exerted by a confined ideal gas," J. Phys. A: Math. Theor. 44, 365001 (2011).
Paradiso, et al., "Energy scavenging for mobile and wireless electronics," IEEE Pervasive Comp. 4, 18-27 (2005).
Qin, Y. et al., "Constant electricity generation in nanostructured silicon by evaporation-driven water flow," Angew. Chem. Int. Ed 59, 10619-10625 (2020).
Reguera et al., "Extracellular electron transfer via microbial nanowires", Nature, vol. 435, Jun. 2005, pp. 1098-1101.
Ren, G. et al., "A facile and sustainable hygroelectric generator using whole-cell Geobacter sulfurreducens," Nano Energy 89, 106361 (2021).
Revil, et al., "Theory of ionic-surface electrical conduction in porous media," Phys. Rev. B 55, 1757-1773 (1997).
Rezende, et al., "Detection of charge distributions in insulator surfaces," J. Phys. Condens. Matter 21, 263002 (2009).
Richter, "Mutational Analysis of Geopilin Function in Geobacter Sulfurreducens", 2011,[retrieved on line Dec. 8, 2016] at <http://scholarworks.umass.edu/open_access_dissertations/378/], 157 pages.
Shen, et al., "Moisture-enabled electricity generation: from physics and materials to self-powered applications," Adv. Mater. 32, Jul. 22, 2003 (2020).
Shih et al., "Tryptophan-Accelerated Electron Flow Through Proteins", Science, vol. 320, Jun. 27, 2008, pp. 1760-1762.
Sisman, et al., "Quantum boundary layer: a non-uniform density distribution of an ideal gas in thermodynamic equilibrium," Phys. Lett. A 362, 16-20 (2007).
Sisman, et al., "The Casimir-like size effects in ideal gases," Phys. Lett. A 320, 360-366 (2004).
Stokes, et al., "A Standard solutions for humidity control at 25° C.," Ind. Eng. Chem. 41, 2013 (1949).
Sun et al,"Flexible polydimethylsiloxane/multi-walled carbon nanotubes membranous metacomposites with negative permittivity," Elsevier, Polymer 125 (2017) 50-57.
Sun, Z. et al., "Emerging design principles, materials, and applications for moisture-enabled electric generation," eScience (2022) https://doi.org/10.1016/j.esci.2021.12.009.
Tan et al., "Synthetic Biological Protein Nanowires with High Conductivity," small 2016, 12, No. 33, 4481-4485.
Tan et al.,"Expressing the Geobacter metallireducens PilA in Geobacter sulfurreducens Yields Pili with Exceptional Conductivity," American Society for Microbiology, Jan./Feb. 2017, vol. 8, Issue 1 e02203-16.
Tang et al, "Effect of pH on Protein Distribution in Electrospun PVA/BSA Composite Nanofibers," 2012 American Chemical Society, 1269-1278.
Tang, et al., "Compilation and evaluation of gas phase diffusion coefficients of reactive trace gases in the atmosphere: vol. 2. Diffusivities of organic compounds, pressure-normalized mean free paths, and average Knudsen numbers for gas uptake calculations," Atoms. Chem. Phys. 15, 5585-5598 (2015).
The Protein Man (https://info.gbiosciences.com/blog/bid/198500/8-protein-tags-explained; 2014).
Tseng et al.,"Digital memory device based on tobacco mosaic virus conjugated with nanoparticles," nature hanotechnology, vol. 1., Oct. 2006, pp. 72-77.
Ueki T., et al., "An *Escherichia coli* Chassis for Production of Electrically Conductive Protein Nanowires," 9(3):647-654 ACS Synth Biol. (2020).
Ueki T., et al., "Decorating the Outer Surface of Microbially Produced Protein Nanowires with Peptides," ACS Synth Biol. X;8{8):1809-1817 (2019).
Ueki, Toshiyuki, et al. "Decorating microbially produced protein nanowires with peptide ligands." bioRxiv (2019): 590224.
Vargas et al., "Aromatic Amino Acids Required for Pili Conductivity and Long-Range Extracellular Electron Transport in Geobacter sulfurreducens", mBio, vol. 4, Issue 2, Mar./Apr. 2013, pp. 1-6.
Walker et al., "Electrically conductive pili from pilin genes of phylogenetically diverse microorganisms," The ISME Journal (2018) 12, 48-58.
Wang et al. "Moisture adsorption-desorption full cycle power generation" Nat Commun 13, 2524 (2022). https://doi.org/10.1038/s41467-022-30156-3 (Year: 2022).
Wu, S., et al., "Regulation of expression of pilA gene in Myxococcus xanthus," Journal of Bacteriology, 179 (24):7748-7758 (1997).
X. Gao et al. "Electric power generation using paper materials", J. Mater. Chem. A, 2019, 7, 20574-20578. (Year: 2019).
Yang, "Synthesis and characterization of the cross-linked PVA/Ti02 composite polymer membrane for alkaline DMFC," Elsivier, Journal of Membrane Science 288 (2007) 51-60.
Yang, Yen-Chun, et al., "PilR enhances the sensitivity of Xanthomonas axonopodis pv. citri to the infection of filamentous bacteriophage Cf," Current Microbiology, 48(4):251-261 (2004).
Yi Cui et al, "Nanowire Nanosensors for Highly Sensitive and Selective Detection of Biological and Chemical Species", Aug. 2021, Science Magazine, vol. 293, pp. 1289-1292. (Year: 2021).
Yin, B., et al., "Bioinspired and bristled microparticles for ultrasensitive pressure and strain sensors," Nat. Commun. 9, 5161 (2018).
Yin, Jun et al. "Hydrovoltaic Energy on the Way" Joule, vol. 4, Issue 9, pp. 1852-1855, Sep. 16, 2020. (Year: 2020).
Zezelj et al., Publishe s Note: From percolating to dense random stick networks: Conductivity model nvestigation [Phys. Rev_ B 86, 134202 (2012)]. Physical Review B 86, 139904(E) (2012).
Zhang et al., "Composite films of nanostructured polyaniline with poly(vinyl alcohol)," Elsevier, Synthetic Metals 12E (2002) 83-89.
Zhang et al., "Electrical and dielectric behaviors and their origins in the three-dimensional polyvinyl alcohol/MWCN-Composites with low percolation threshold," Elsevier, Carbon 47 (2009) 1311-1320.
Zhang, et al., "Digestion of ambient humidity for energy generation," Joule 4, 2532-2536 (2020).
Zhang, et al., "Emerging hydrovoltaic technology," Nat. Nanotechnol. 13, 1109-1119 (2018).
Zhang, et al., "Sub-10 nm wide cellulose nanofibers for ultrathin nanoporous membranes with high organic permeation," Adv. Funct. Mater. 26, 792-800 (2016).
Adhikari et al., "Conductivity of individual Geobacter pili," RSC Advances., 2016, 6, 8354-8357.
Al-abadleh, et al., "FT-IT study of water adsorption on aluminum oxide surfaces," Langmuir 19, 341-347 (2003).
Amrin et al., "Electrical properties and conduction mechanism in carboxylfunclionalized multiwalled carbon hanolubes/poly(vinyl alcohol) composites," J Maler Sci (2016) 51:2453-2464.
Bai, J. et al., "Sunlight-coordinated high-performance moisture power in natural condition," Adv. Mater. (2022) https://doi.org/10.1002/adma.202103897.
Balberg et al., "Excluded volume and its relation to the onset of percolation," Physical Review B, vol. 30, No. 7, Oct. 1, 1984.
Bauhofer et al, "A review and analysis of electrical percolation in carbon nanolube polymer composites," Elsevier, Composites Science and Technology 69 (2009) 1486-1498.
Byrne et al., "Recent Advances in Research on Carbon Nanolube-Polymer Composites," Advanced Materials, 2010,22, 1672-1688.
Celzard et al,"Critical concentration in percolating systems containing a high-aspect-ratio filler," Physical Review 8, vol. 53, No. 10, Mar. 1, 1996.
Chandrakishore et al, "Facile synthesis of carbon nanolubes and their use in the fabrication of resistive switching memory devices," RSC Advances, 2014, 4, 9905-9911.

(56) References Cited

OTHER PUBLICATIONS

Chen et al., "Electrical Conductivity of Polymer Blends of Poly(3,4-ethylenedioxythiophene) : Poly (styrenesulfonate) :N-Methyl-2-pyrrolidinone and Polyvinyl Alcohol," Journal of Applied Polymer Science, vol. 125, 3134-3141 (2012).
Cheng, H. et al., "Spontaneous power source in ambient air of a well-directionally reduced graphene oxide bulk," Energy Environ. Sci. 11, 2839 (2018).
Childers et al., "Geobacter metallireducens accesses insoluble Fe(III) oxide by chemotaxis" Nature, vol. 416, Apr. 18, 2002, pp. 767-769.
Cho et al.,"Synthesis and electrical properties of polymer composites with polyaniline nanoparticles," Elsevier,Materials Science and Engineering C 24 (2004) 15-18.
Coppi et al., "Development of a Genetic System for Geobacter sulfurreducens", Applied and Environmental Microbiology, vol. 67, No. 7, Jul. 2001, pp. 3180-3187.
Cui, Yi, et al, "Nanowire Nanosensors for Highly Sensitive and Selective Detection of Biological and Chemical Species", Aug. 2021, Science Magazine, vol. 293, pp. 1289-1292. (Year: 2021).
Fu, T. et al., "Self-sustained green neuromorphic interfaces," Nat. Commun. 12, 3351 (2021).
Fu, Tianda, et al, "Bioinspired bio-voltage memristors", Nature Communications, 2020, Article pp. 1-10 (Year: 2020).
Gangopadhyay et al., "Polyaniline-poly(vinyl alcohol) conducting composite: material with easy processability 2nd novel application potential," Elsevier, Synthetic Metals 123 (2001) 21-31.
Gerald F. Audette et al, "Protein Nanotubes: From Bio-nanotech towards Medical Applications", Jun. 2019, Biomedicines Journal, vol. 7/46. (Year: 2019).
Gielen, et al., "The role of renewable energy in the global energy transformation," Energy Strategy Rev. 24, 38-50 (2019).
Green et al, "Conductive Hydrogels: Mechanically Robust Hybrids for Use as Biomalerials," Macromolecular Bioscience, 2012, 12, 494-501.
Guo et al, "Flexible transparent conductors based on metal nanowire networks," Elsevier, Materials Today, vol. 18, No. 3, Apr. 2015.
Han, et al., "Facile synthesis of poly(3,4-ethylenedioxythiophene) nanofibers from an aqueous surfactant solution," Small 2, 1164-1169 (2006).
Hanikel "MOF water harvesters", Nature Nanotechnology, vol. 15, pp. 348-355 (2020). (Year: 2020).
Hanikel et al. "Rapid cycling and exceptional yield in a metal-organic framework water harvester", ACS Cent. Sci. 5, pp. 1699-1706 (2019). (Year: 2019).
Ho, et al., "Gas Transport in Porous Media," (Springer, 2006).
https://en.wikipedia.org/wiki/Adsorption (Year: 2024).
Huang et al., "Interface-mediated hygroelectric generator with an output voltage approaching 1.5 volts", Nat Commun. Oct. 9, 2018; 9(1):4166. doi: 10.1038/s41467-018-06633-z. PMID: 30301892; PMCID: PMC6177432. (Year: 2018).
Jerry A. Fereira et al, "Tunneling explains efficient electron transport via protein junctions", Weizmann Institute of SCience Reports, Nov. 2017, vol. 114, No. 20 (Year: 2017).
Kaunda, et al., "Hydropower in the context of sustainable energy supply: a review of technologies and challenges," ISRN Renewable Energy 2012, 730631 (2012).
Kim et al. "Water harvesting from air with metal-organic frameworks powered by natural sunlight" Science Apr. 13, 2017 vol. 356, Issue 6336, pp. 430-434. DOI: 10.1126/science.aam8743 (Year: 2017).
Kumar, Anish, et al, "Protein Biosensors Based on Polymer Nanowires, Carbon Nanotubes and Zinc Oxide Nanorods", Sensors Journal, May 2011, 5087-5111 {Year: 2011).
Langmuir, "Vapor pressures, evaporation, condensation and adsorption," J. Am. Chem. Soc. 54, 2798-2832 (1932).
Li et al, "Ordered multiphase polymer nanocomposites for high-performance solid-slate supercapacitors," Elsevier, Composites: Part B 71 (2015), 40-44.
Liu et al, "Flexible supercapacitor sheets based on hybrid nanocomposite materials," Elsevier, Nano Energy (2013) 133-137.
Liu et al., "A Geobacter sulfurreducens Strain Expressing Pseudomonas aeruginosa Type IV Pili Localizes OmcS on Pili but Is Deficient in Fe(III) Oxide Reduction and Current Production", Applied and Environmental Microbiology, vol. 80, No. 3, Feb. 2014, pp. 1219-1224 (cited in specification on p. 14).
Liu X., et al., "Power Generation from Ambient Humidity Using Protein Nanowires," Nature; 578: 550-554 (2020).
Liu, et al., "Induced potential in porous carbon films through water vapor absorption," Angew. Chem. Int. Ed. 55, 8003-8007 (2016).
Liu, T. et al, "Regulating the interlayer spacing of graphene oxide membranes and enhancing their stability by use of PACI," Environ. Sci. Technol. 53, 11949-11959 (2019).
Liu, X. et al., "Multifunctional protein nanowire humidity sensors for green wearable electronics," Adv. Electron. Mater. 6, Jul. 21, 2000 (2020).
Lovely,D., et al., "Geobacter Protein Nanowires", Front. Microbial. 10, 2078 (2019).
Lovley et al., "Seeing is believing: novel imaging techniques help clarify microbial nanowire structure and function", Environmental microbiology, vol. 17, Issue 7, 2015, pp. 2209-2215.
Lovley, "e-Biologics: Fabrication of Sustainable Electronics with 'Green' Biological Materials," American Society for Microbiology, May/Jun. 2017, vol. 8, Issue 3 e00695-17.
Lovley, "Electrically conductive pili: Biological function and potential applications in electronics," Science Direct, Current Opinion in Electrochemistry 2017, 4: 190-198.
Lovley, et al., "Intrinsically conductive microbial nanowires for 'green' electronics with novel functions," Trends Biotechnol. 39, 940-952 (2021).
Makhlouki et al., "Transport Properties in Polypyrrole-PVA Composites: Evidence for Hopping Conduction," Journal of Applied Polymer Science, vol. 44, 443-446 (1992).
Malhofer et al., "Direct visualization of percolation paths in carbon nanolube/polymer composites," Elsevier, Organic Electronics 45 (2017) 151-158.
Malvankar et al., "Lack of cytochrome involvement in long-range electron transport through conductive biofilms and nanowires of Geobacter sulfurreducens", Energy & Environmental Science, vol. 5, 2012, pp. 8651-8686.
Malvankar et al., "Structural Basis for Metallic-Like Conductivity in Microbial Nanowires," Mar./Apr. 2015 mBio vol. 6 Issue 2 e00084-15.
Malvankar et al., "Tunable metallic-like conductivity in microbial nanowires", Nature Nanotechnology, vol. 6, Sep. 2011, pp. 573-579.

* cited by examiner

Typical AGGAGGNNNNNNNNNATG (SEQ ID NO:3)

RBS 7-9 bp Met

>hofB

Wild-type: ACTAAGGAGCGGCAATG (SEQ ID NO: 4)

Modified: AGGAAGGAGCGGCAATG (SEQ ID NO: 5)

>hofM

Wild-type: ATATACCCGTCAGAGTG (SEQ ID NO: 6)

Modified: AGAAGGCCGTCAGAGTG (SEQ ID NO: 7)

>ppdA

Wild-type: TCCATACTGCCGGCATG (SEQ ID NO: 8)

Modified: AGGAGACTGCCGGCATG (SEQ ID NO: 9)

FIG. 1C

```
Between hofc and hofM
Original: CCATGGAAGGCAAGCCAGACGCATTGATATACCCGTCAGA (HofM) (SEQ ID NO:10)
Modified:                                TCTAGAAGGCCGTCAGA (HofM) (SEQ ID NO:11)

Between hofQ and ppdA
Original: GGCGCGCCTTCTCCTCGCTCCATACTGCCGGC (PpdA) (SEQ ID NO:12)
Modified:                AAGCTTAGGAGACTGCCGGC (PpdA) (SEQ ID NO:13)

Between ppdC and gspO
Original: CTCGAGGTCCTTCAGGGAGCAACAATA (GspO) (SEQ ID NO:14)
Modified:                  CAGGGAGCAACAATA (GspO) (SEQ ID NO:15)
```

FIG. 1D

>Wild-type PpdD
MDKQRGFTLIELMVVIGIIAILSAIGIPAYQNYLRKAALTDMLQTFVPYRTAVELCALEH
GGLDTCDGGSNGIPSPTTTRYVSAMSVAKGVVSLTGQESLNGLSVVMTPGWDNANGVTGW
ARNCNIQSDSALQQACEDVFRFDDAN (SEQ ID NO:44)

>PpdD-HA
MDKQRGFTLIELMVVIGIIAILSAIGIPAYQNYLRKAALTDMLQTFVPYRTAVELCALEH
GGLDTCDGGSNGIPSPTTTRYVSAMSVAKGVVSLTGQESLNGLSVVMTPGWDNANGVTGW
ARNCNIQSDSALQQACEDVFRFDDANYPYDVPDYA (SEQ ID NO:45)

FIG. 1E

>Gs-PilA
MDKQRGFTLIELLIVVAIIGILAAIAIPQFSAYRVKAYNSAASSDLRNLKTALESA
FADDQTYPPES (SEQ ID NO:18)

FIG. 1F

SEQUENCE LISTING

<160> NUMBER OF SEQ ID NOS: 45

<210> SEQ ID NO 1
<211> LENGTH: 16
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 7, 8, 9, 10, 11, 12, 13
<223> OTHER INFORMATION: n = A,T,C or G

<400> SEQUENCE: 1
aggaggnnnn nnnatg 16

<210> SEQ ID NO 2
<211> LENGTH: 17
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 7, 8, 9, 10, 11, 12, 13, 14
<223> OTHER INFORMATION: n = A,T,C or G

<400> SEQUENCE: 2
aggaggnnnn nnnnatg 17

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 7, 8, 9, 10, 11, 12, 13, 14, 15
<223> OTHER INFORMATION: n = A,T,C or G

<400> SEQUENCE: 3
aggaggnnnn nnnnnatg 18

<210> SEQ ID NO 4
<211> LENGTH: 17
<212> TYPE: DNA
<213> ORGANISM: Escherichia coli

<400> SEQUENCE: 4
actaaggagc ggcaatg 17

<210> SEQ ID NO 5
<211> LENGTH: 17
<212> TYPE: DNA
<213> ORGANISM: Artificial Sequence
<220> FEATURE:
<223> OTHER INFORMATION: Oligonucleotide

<400> SEQUENCE: 5
aggaaggagc ggcaatg 17

<210> SEQ ID NO 6
<211> LENGTH: 17
<212> TYPE: DNA
<213> ORGANISM: Escherichia coli

<400> SEQUENCE: 6
atatacccgt cagagtg 17

<210> SEQ ID NO 7
<211> LENGTH: 17
<212> TYPE: DNA
<213> ORGANISM: Artificial Sequence
<220> FEATURE:
<223> OTHER INFORMATION: Oligonucleotide

<400> SEQUENCE: 7
agaaggccgt cagagtg 17

<210> SEQ ID NO 8
<211> LENGTH: 17
<212> TYPE: DNA
<213> ORGANISM: Escherichia coli

<400> SEQUENCE: 8
tccatactgc cggcatg 17

<210> SEQ ID NO 9
<211> LENGTH: 17
<212> TYPE: DNA
<213> ORGANISM: Artificial Sequence
<220> FEATURE:
<223> OTHER INFORMATION: Oligonucleotide

<400> SEQUENCE: 9
aggagactgc cggcatg 17

<210> SEQ ID NO 10
<211> LENGTH: 40
<212> TYPE: DNA
<213> ORGANISM: Escherichia coli

<400> SEQUENCE: 10
ccatggaagg caagccagac gcattgatat acccgtcaga 40

<210> SEQ ID NO 11
<211> LENGTH: 17
<212> TYPE: DNA
<213> ORGANISM: Artificial Sequence
<220> FEATURE:
<223> OTHER INFORMATION: Oligonucleotide

<400> SEQUENCE: 11
tctagaaggc cgtcaga 17

<210> SEQ ID NO 12
<211> LENGTH: 32
<212> TYPE: DNA
<213> ORGANISM: Escherichia coli

<400> SEQUENCE: 12
ggcgcgcctt ctcctcgctc catactgccg gc 32

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide

<400> SEQUENCE: 13

-continued

```
aagcttagga gactgccggc                                                20


<210> SEQ ID NO 14
<211> LENGTH: 27
<212> TYPE: DNA
<213> ORGANISM: Escherichia coli

<400> SEQUENCE: 14

ctcgaggtcc ttcagggagc aacaata                                        27


<210> SEQ ID NO 15
<211> LENGTH: 15
<212> TYPE: DNA
<213> ORGANISM: Artificial Sequence
<220> FEATURE:
<223> OTHER INFORMATION: Oligonucleotide

<400> SEQUENCE: 15

cagggagcaa caata                                                     15


<210> SEQ ID NO 16
<211> LENGTH: 61
<212> TYPE: PRT
<213> ORGANISM: Geobacter sulfurreducens

<400> SEQUENCE: 16

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser
    50                  55                  60


<210> SEQ ID NO 17
<211> LENGTH: 6
<212> TYPE: PRT
<213> ORGANISM: Escherichia coli

<400> SEQUENCE: 17

Met Asp Lys Gln Arg Gly
1               5


<210> SEQ ID NO 18
<211> LENGTH: 67
<212> TYPE: PRT
<213> ORGANISM: Artificial Sequence
<220> FEATURE:
<223> OTHER INFORMATION: Modified Geobacter sulfurreducens PilA

<400> SEQUENCE: 18

Met Asp Lys Gln Arg Gly Phe Thr Leu Ile Glu Leu Leu Ile Val Val
1               5                   10                  15

Ala Ile Ile Gly Ile Leu Ala Ala Ile Ala Ile Pro Gln Phe Ser Ala
            20                  25                  30

Tyr Arg Val Lys Ala Tyr Asn Ser Ala Ala Ser Ser Asp Leu Arg Asn
        35                  40                  45

Leu Lys Thr Ala Leu Glu Ser Ala Phe Ala Asp Asp Gln Thr Tyr Pro
    50                  55                  60

Pro Glu Ser
65
```

<210> SEQ ID NO 19
<211> LENGTH: 4
<212> TYPE: PRT
<213> ORGANISM: Artificial Sequence
<220> FEATURE:
<223> OTHER INFORMATION: Histidine (His) Tag

<400> SEQUENCE: 19

His His His His
1

<210> SEQ ID NO 20
<211> LENGTH: 5
<212> TYPE: PRT
<213> ORGANISM: Artificial Sequence
<220> FEATURE:
<223> OTHER INFORMATION: Histidine (His) Tag

<400> SEQUENCE: 20

His His His His His
1               5

<210> SEQ ID NO 21
<211> LENGTH: 6
<212> TYPE: PRT
<213> ORGANISM: Artificial Sequence
<220> FEATURE:
<223> OTHER INFORMATION: Histidine (His) Tag

<400> SEQUENCE: 21

His His His His His His
1               5

<210> SEQ ID NO 22
<211> LENGTH: 7
<212> TYPE: PRT
<213> ORGANISM: Artificial Sequence
<220> FEATURE:
<223> OTHER INFORMATION: Histidine (His) Tag

<400> SEQUENCE: 22

His His His His His His His
1               5

<210> SEQ ID NO 23
<211> LENGTH: 8
<212> TYPE: PRT
<213> ORGANISM: Artificial Sequence
<220> FEATURE:
<223> OTHER INFORMATION: Histidine (His) Tag

<400> SEQUENCE: 23

His His His His His His His His
1               5

<210> SEQ ID NO 24
<211> LENGTH: 9
<212> TYPE: PRT
<213> ORGANISM: Artificial Sequence
<220> FEATURE:
<223> OTHER INFORMATION: Histidine (His) Tag

<400> SEQUENCE: 24

His His His His His His His His His
1               5

<210> SEQ ID NO 25
<211> LENGTH: 10
<212> TYPE: PRT
<213> ORGANISM: Artificial Sequence
<220> FEATURE:
<223> OTHER INFORMATION: Histidine (His) Tag

<400> SEQUENCE: 25

His His His His His His His His His His
1 5 10

<210> SEQ ID NO 26
<211> LENGTH: 7
<212> TYPE: PRT
<213> ORGANISM: Artificial Sequence
<220> FEATURE:
<223> OTHER INFORMATION: Histidine (His) Tag

<400> SEQUENCE: 26

His His His His His His Cys
1 5

<210> SEQ ID NO 27
<211> LENGTH: 9
<212> TYPE: PRT
<213> ORGANISM: Artificial Sequence
<220> FEATURE:
<223> OTHER INFORMATION: HA Tag

<400> SEQUENCE: 27

Tyr Pro Tyr Asp Val Pro Asp Tyr Ala
1 5

<210> SEQ ID NO 28
<211> LENGTH: 29
<212> TYPE: DNA
<213> ORGANISM: Artificial Sequence
<220> FEATURE:
<223> OTHER INFORMATION: Oligonucleotide

<400> SEQUENCE: 28
ttcagatctg caaatattct gaaatgagc 29

<210> SEQ ID NO 29
<211> LENGTH: 30
<212> TYPE: DNA
<213> ORGANISM: Artificial Sequence
<220> FEATURE:
<223> OTHER INFORMATION: Oligonucleotide

<400> SEQUENCE: 29
ttctctagag gggaattgtt atccgctcac 30

<210> SEQ ID NO 30
<211> LENGTH: 33
<212> TYPE: DNA
<213> ORGANISM: Artificial Sequence
<220> FEATURE:
<223> OTHER INFORMATION: Oligonucleotide

<400> SEQUENCE: 30
tctgagctca ggaaggagcg gcaatgaata ttc 33

<210> SEQ ID NO 31
<211> LENGTH: 28
<212> TYPE: DNA

<213> ORGANISM: Artificial Sequence
<220> FEATURE:
<223> OTHER INFORMATION: Oligonucleotide

<400> SEQUENCE: 31
atctctagat tatcccatcc cactcatc 28

<210> SEQ ID NO 32
<211> LENGTH: 35
<212> TYPE: DNA
<213> ORGANISM: Artificial Sequence
<220> FEATURE:
<223> OTHER INFORMATION: Oligonucleotide

<400> SEQUENCE: 32
atctctagaa ggccgtcaga gtgacgggtg ataag 35

<210> SEQ ID NO 33
<211> LENGTH: 27
<212> TYPE: DNA
<213> ORGANISM: Artificial Sequence
<220> FEATURE:
<223> OTHER INFORMATION: Oligonucleotide

<400> SEQUENCE: 33
tctaagctta ctcactggaa accagtc 27

<210> SEQ ID NO 34
<211> LENGTH: 36
<212> TYPE: DNA
<213> ORGANISM: Artificial Sequence
<220> FEATURE:
<223> OTHER INFORMATION: Oligonucleotide

<400> SEQUENCE: 34
tctaagctta ggagactgcc ggcatgaaaa cacaac 36

<210> SEQ ID NO 35
<211> LENGTH: 41
<212> TYPE: DNA
<213> ORGANISM: Artificial Sequence
<220> FEATURE:
<223> OTHER INFORMATION: Oligonucleotide

<400> SEQUENCE: 35
gtcattattg ttgctccctg ctactgacga ttcggacaat g 41

<210> SEQ ID NO 36
<211> LENGTH: 41
<212> TYPE: DNA
<213> ORGANISM: Artificial Sequence
<220> FEATURE:
<223> OTHER INFORMATION: Oligonucleotide

<400> SEQUENCE: 36
cattgtccga atcgtcagta gcagggagca acaataatga c 41

<210> SEQ ID NO 37
<211> LENGTH: 29
<212> TYPE: DNA
<213> ORGANISM: Artificial Sequence
<220> FEATURE:
<223> OTHER INFORMATION: Oligonucleotide

<400> SEQUENCE: 37
tctctcgagt tatctgcaag cacagatcc 29

<210> SEQ ID NO 38
<211> LENGTH: 29
<212> TYPE: DNA
<213> ORGANISM: Artificial Sequence
<220> FEATURE:
<223> OTHER INFORMATION: Oligonucleotide

<400> SEQUENCE: 38
tctcatatgg acaagcaacg cggttttac 29

<210> SEQ ID NO 39
<211> LENGTH: 58
<212> TYPE: DNA
<213> ORGANISM: Artificial Sequence
<220> FEATURE:
<223> OTHER INFORMATION: Oligonucleotide

<400> SEQUENCE: 39
tctgagctct tacgcgtagt ccggcacgtc gtacgggtag ttggcgtcat caaagcgg 58

<210> SEQ ID NO 40
<211> LENGTH: 43
<212> TYPE: DNA
<213> ORGANISM: Artificial Sequence
<220> FEATURE:
<223> OTHER INFORMATION: Oligonucleotide

<400> SEQUENCE: 40
tctcatatgg acaagcaacg cggtttcacc cttatcgagc tgc 43

<210> SEQ ID NO 41
<211> LENGTH: 29
<212> TYPE: DNA
<213> ORGANISM: Artificial Sequence
<220> FEATURE:
<223> OTHER INFORMATION: Oligonucleotide

<400> SEQUENCE: 41
tctgagctct taactttcgg gcggatagg 29

<210> SEQ ID NO 42
<211> LENGTH: 222
<212> TYPE: DNA
<213> ORGANISM: Artificial Sequence
<220> FEATURE:
<223> OTHER INFORMATION: Polynucleotide

<400> SEQUENCE: 42
atggacaagc aacgcggttt cacccttatc gagctgctga tcgtcgttgc gatcatcggt 60
attctcgctg caattgcgat tccgcagttc tcggcgtatc gtgtcaaggc gtacaacagc 120
gcggcgtcaa gcgacttgag aaacctgaag actgctcttg agtccgcatt tgctgatgat 180
caaacctatc cgcccgaaag tcaccaccac caccaccact aa 222

<210> SEQ ID NO 43
<211> LENGTH: 73
<212> TYPE: PRT
<213> ORGANISM: Artificial Sequence
<220> FEATURE:
<223> OTHER INFORMATION: Modified Geobacter sulfurreducens PilA

<400> SEQUENCE: 43

Met Asp Lys Gln Arg Gly Phe Thr Leu Ile Glu Leu Leu Ile Val Val
1 5 10 15

```
Ala Ile Ile Gly Ile Leu Ala Ala Ile Ala Ile Pro Gln Phe Ser Ala
            20                  25                  30

Tyr Arg Val Lys Ala Tyr Asn Ser Ala Ala Ser Ser Asp Leu Arg Asn
        35                  40                  45

Leu Lys Thr Ala Leu Glu Ser Ala Phe Ala Asp Asp Gln Thr Tyr Pro
    50                  55                  60

Pro Glu Ser His His His His His His
65                  70
```

<210> SEQ ID NO 44
<211> LENGTH: 146
<212> TYPE: PRT
<213> ORGANISM: Escherichia coli

<400> SEQUENCE: 44

```
Met Asp Lys Gln Arg Gly Phe Thr Leu Ile Glu Leu Met Val Val Ile
1               5                   10                  15

Gly Ile Ile Ala Ile Leu Ser Ala Ile Gly Ile Pro Ala Tyr Gln Asn
            20                  25                  30

Tyr Leu Arg Lys Ala Ala Leu Thr Asp Met Leu Gln Thr Phe Val Pro
        35                  40                  45

Tyr Arg Thr Ala Val Glu Leu Cys Ala Leu Glu His Gly Gly Leu Asp
    50                  55                  60

Thr Cys Asp Gly Gly Ser Asn Gly Ile Pro Ser Pro Thr Thr Thr Arg
65                  70                  75                  80

Tyr Val Ser Ala Met Ser Val Ala Lys Gly Val Val Ser Leu Thr Gly
                85                  90                  95

Gln Glu Ser Leu Asn Gly Leu Ser Val Val Met Thr Pro Gly Trp Asp
            100                 105                 110

Asn Ala Asn Gly Val Thr Gly Trp Ala Arg Asn Cys Asn Ile Gln Ser
        115                 120                 125

Asp Ser Ala Leu Gln Gln Ala Cys Glu Asp Val Phe Arg Phe Asp Asp
    130                 135                 140

Ala Asn
145
```

<210> SEQ ID NO 45
<211> LENGTH: 155
<212> TYPE: PRT
<213> ORGANISM: Artificial Sequence
<220> FEATURE:
<223> OTHER INFORMATION: PpdD-HA

<400> SEQUENCE: 45

```
Met Asp Lys Gln Arg Gly Phe Thr Leu Ile Glu Leu Met Val Val Ile
1               5                   10                  15

Gly Ile Ile Ala Ile Leu Ser Ala Ile Gly Ile Pro Ala Tyr Gln Asn
            20                  25                  30

Tyr Leu Arg Lys Ala Ala Leu Thr Asp Met Leu Gln Thr Phe Val Pro
        35                  40                  45

Tyr Arg Thr Ala Val Glu Leu Cys Ala Leu Glu His Gly Gly Leu Asp
    50                  55                  60

Thr Cys Asp Gly Gly Ser Asn Gly Ile Pro Ser Pro Thr Thr Thr Arg
65                  70                  75                  80

Tyr Val Ser Ala Met Ser Val Ala Lys Gly Val Val Ser Leu Thr Gly
                85                  90                  95
```

-continued

```
Gln Glu Ser Leu Asn Gly Leu Ser Val Val Met Thr Pro Gly Trp Asp
            100                 105                 110

Asn Ala Asn Gly Val Thr Gly Trp Ala Arg Asn Cys Asn Ile Gln Ser
        115                 120                 125

Asp Ser Ala Leu Gln Gln Ala Cys Glu Asp Val Phe Arg Phe Asp Asp
    130                 135                 140

Ala Asn Tyr Pro Tyr Asp Val Pro Asp Tyr Ala
145                 150                 155
```

EXPRESSION OF ELECTRICALLY CONDUCTIVE PROTEIN NANOWIRES IN *ESCHERICHIA COLI*

RELATED APPLICATION

This application is the U.S. National Stage of International Application No. PCT/US2020/061609, filed on Nov. 20, 2020, published in English, which claims the benefit of U.S. Provisional Application No. 62/938,913, filed on Nov. 21, 2019. The entire teachings of the above applications are incorporated herein by reference.

GOVERNMENT SUPPORT

This invention was made with government support under Grant No. CMMI-1921839 awarded by the National Science Foundation. The government has certain rights in the invention.

INCORPORATION BY REFERENCE OF MATERIAL IN ASCII TEXT FILE

This application incorporates by reference the Sequence Listing contained in the following ASCII text file being submitted concurrently herewith:

a) File name: 46821019002_Sequence_Listing.txt; created May 11, 2022, 12,252 Bytes in size.

BACKGROUND

Electrically conductive protein nanowires (e-PNs) show promise as revolutionary, sustainably produced, electronic materials that are robust, biocompatible, and readily adapted for sensing applications (Creasey et al., 2018; Gutermann and Gazit, 2018; Ing et al., 2018a; Lovley, 2017a; Lovley, 2017b; Sun et al., 2018; Ueki et al., 2019). However, their implementation in electronic devices, for example, has been limited due to a lack of methods for mass production. In vitro assembly of peptides into conductive nanofilaments is feasible (Creasey et al., 2015; Ing et al., 2018b); however, the filaments tend to agglomerate into gels at high peptide concentrations, limiting the possibilities for large-scale fabrication. Additionally, synthesis of the peptide monomers required for in vitro assembly is expensive, potentially limiting protein nanowire affordability and applications.

SUMMARY

There is a critical need for host cells and methods that are better suited for large-scale e-PN production.

The invention disclosed herein is based, in part, on the discovery that e-PNs can be produced in *E. coli* cells and collected using a filtration method. Accordingly, the invention generally relates to host cells, polynucleotides and methods for producing non-native e-PNs.

One aspect of the invention relates to a genetically modified aerobic bacterium, wherein the bacterium comprises a polynucleotide encoding an electrically conductive fusion protein that comprises a non-native pilin monomer.

In some aspects, the bacterium is non-pathogenic. In some aspects, the bacterium is an *Escherichia coli* (*E. coli*) cell.

In some embodiments, the bacterium further comprises a polynucleotide sequence encoding a wildtype pilus assembly protein or a variant thereof. In some embodiments, the pilus assembly protein is an *E. coli* type IV pilus assembly protein. In some embodiments, the *E. coli* type IV pilus assembly protein is horn, hofC, hofM, hofN, hofO, hovP, hofQ, ppdA, ppdB, ygdB, ppdC or gspO, or a combination thereof.

In some embodiments, the non-native pilin monomer is a *Geobacter* pilin monomer. In some embodiments, the *Geobacter* pilin monomer comprises an amino acid sequence that has at least 90% sequence identity to the wildtype *Geobacter sulfurreducens* PilA monomer (SEQ ID NO:16).

Another aspect of the invention relates to a polynucleotide that comprises an artificial operon that comprises a cluster of two or more polynucleotide sequences, each polynucleotide sequence encoding a pilus assembly protein.

In some embodiments, the artificial operon is the lac operon. In some embodiments, the artificial operon comprises hofB-hofC-hofM-hofN-hofO-hovP-hofQ-ppdA-ppdB-ygdB-ppdC-gspO or a variant thereof. In some embodiments, the pilus assembly protein is hofB, hofC, hofM, hofN, hofO, hovP, hofQ, ppdA, ppdB, ygdB, ppdC or gspO, or a combination thereof.

In some embodiments, the polynucleotide is operably linked to an expression control polynucleotide sequence. In some embodiments, the expression control polynucleotide sequence comprises a strong *E. coli* promoter.

Another aspect of the invention relates to a method of producing electrically conductive protein nanowires, comprising the steps of:

a) placing a bacterium described herein in a culture medium conditioned for producing the pili;
b) culturing the bacterium for a time sufficient to produce a desired quantity of the pili; and
c) isolating the pili from the culture medium, thereby producing the electrically conductive protein nanowires.

In some embodiments, the method further comprises culturing the host cell in the presence of an inducing molecule.

In some embodiments, isolating the pili from the culture medium comprises filtering the culture medium.

In some embodiments, the culture medium is filtered using a filter having a molecular weight cutoff of about 90 kDa to about 110 kDa.

In some embodiments, the culture medium is filtered using a membrane filter made from polyethersulfone.

Another aspect of the invention relates to a method of producing electrically conductive protein nanowires, comprising the steps of:

a) introducing a polynucleotide into a genetically modified aerobic bacterium described herein, wherein the polynucleotide encodes an electrically conductive fusion protein that comprises a non-native pilin monomer described herein;
b) placing the bacterium in a culture medium conditioned for producing the pili;
c) culturing the bacterium for a time sufficient to produce a desired quantity of the pili; and
d) isolating the pili from the culture medium, thereby producing the electrically conductive protein nanowires.

Another aspect of the invention relates to an electrically conductive protein nanowire produced using a method described herein.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 1A-1F depict construction of a non-limiting example of a type IV pilus assembly system in *E. coli*. FIG. 1A depicts an expression vector comprising genes encoding *E. coli* type IV pilus assembly proteins, lac repressor gene (lad) and kanamycin-resistance gene (kan$^R$). FIG. 1B depicts an artificial operon composed of a cluster of genes encoding *E. coli* type IV pilus assembly proteins. FIG. 1C depicts modifications of ribosome binding sites (RBS) of hofB, hofM and ppdA. Ribosome binding sequences are dotted underlined. FIG. 1D depicts modification of intergenic regions within the artificial operon. Restriction enzyme sites are underlined, and ribosome binding sequences are dotted underlined. FIG. 1E depicts amino acid sequences of the wild-type and HA-tagged PpdD (PpdD-HA). Signal sequences are underlined, and HA tag is dotted underlined. FIG. 1F depicts the amino acid sequence of modified *Geobacter sulfurreducens* pilin PilA (Gs-PilA) with signal sequence from *E. coli* PpdD gene (underlined).

FIG. 2A is a Western blot with anti-HA-tag antibody showing the expression of PpdD-HA pilin monomer. FIG. 2B is Western blot with anti-PilA antibody showing the expression of a modified *G. sulfurreducens* PilA monomer. Strains with the pilin genes are designated with (+). Control strains without the pilin genes are designated (−). Samples from whole-cell extracts (CE) and the pili preparations (PP) were examined. Lanes designated M show molecular weight standard markers.

FIG. 3A is a transmission electron micrograph of e-PNs harvested from *E. coli* strain GPN. FIG. 3B compares the conductance of films of e-PNs expressed in *E. coli* with e-PNs expressed in wild-type *Geobacter sulfurreducens* and the Aro-5 strain of *G. sulfurreducens*. The results are the means and standard deviation of triplicate measurements on each nanoelectrode array for at least three independent nanoelectrode arrays.

FIG. 4A is an amplitude image of two e-PNs in amplitude modulation mode. FIG. 4B is a height image of each e-PN. FIG. 4C is a cross-section line trace showing the height of two individual e-PNs, designated in FIGS. 4A and 4B by the red line, demonstrating a height (diameter) of ~3 nm. FIG. 4D shows the current-voltage response of nine individual measurements (three measurements on each of three e-PNs).

FIG. 5A is a Western dot blot with an anti-6His tag antibody showing expression of *E. coli* pilin PpdD (left) or *G. sulfurreducens* PilA (right) with a His-tag at the C-terminus end in *E. coli* strain GPN. FIG. 5B shows is a Western blot with an anti-6His tag antibody. Total cell lysates from *E. coli* without pili (control, lane C), *E. coli* expressing *E. coli* PpdD-6His pili (lane E), or *E. coli* expressing *Geobacter* PilA-6His pili (lane G) were separated on SDS-PAGE. The proteins were transferred from the gel to membrane and analyzed by Western blot with 6His antibody. Lane M is protein standard markers and their sizes are shown at left. FIG. 5C shows ELISA assay for nickel binding demonstrated more binding of nickel (increased absorbance at 450 nm) by e-PNs displaying a His-tag (+6His) than e-PNs with the same amino acid sequence with the exception of no terminal histidines (−6His).

FIG. 6A shows that the diameter of the device is 4 mm with each gold pad measuring 1 mm×1 mm. FIG. 6B shows close up detail of the interdigitated nanoelectrodes show the distance between SMU1-SMU2 and SMU3—Ground to be 3 μm, and the distance between SMU2 and SMU3 is 15 μm. The e-PNs when dropcast, bridge the gap between the interdigitated electrodes, allowing voltage sweeps to calculate the conductance values from the difference in current measured across the inner electrodes.

DETAILED DESCRIPTION

Figure 1A:
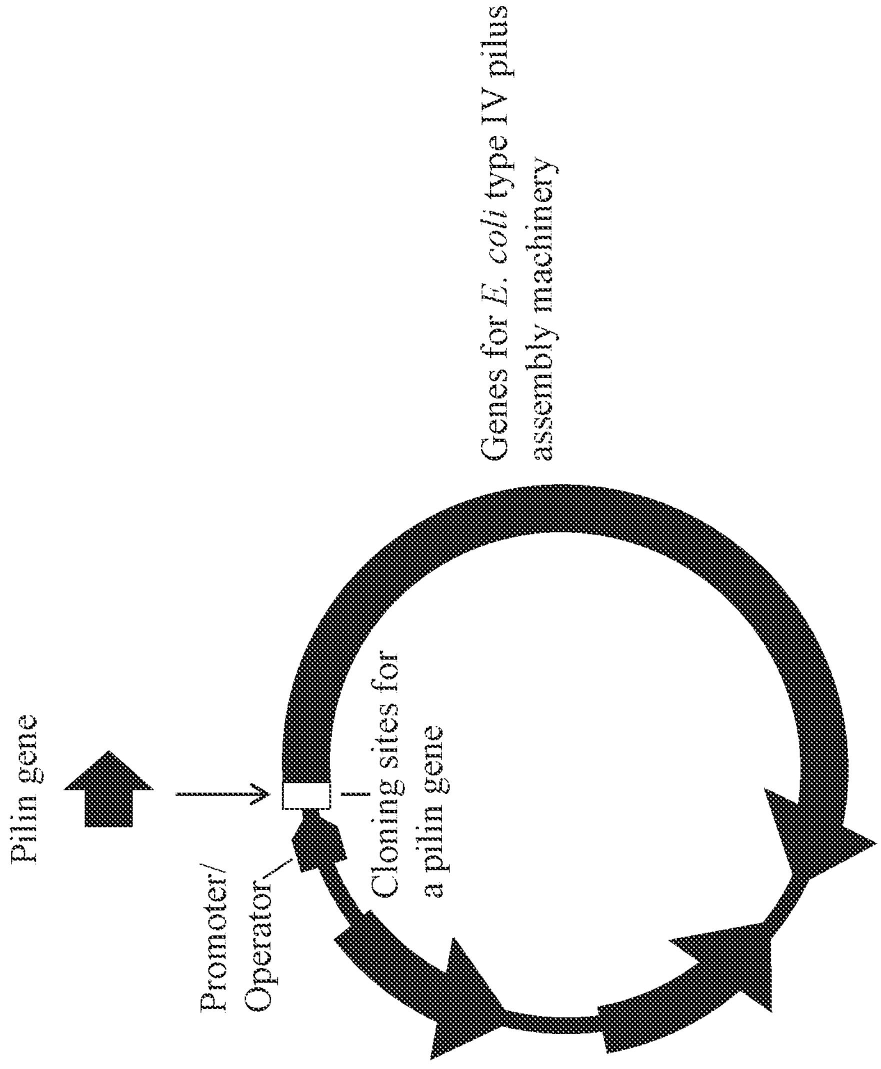

A description of example embodiments follows.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly-used dictionaries, should be interpreted as having a meaning that is consistent with their meaning in the context of the relevant art and/or as otherwise defined herein.

The terminology used herein is for the purpose of describing particular embodiments only and is not intended to be limiting.

As used herein, the indefinite articles "a," "an" and "the" should be understood to include plural reference unless the context clearly indicates otherwise.

The terms "protein," "peptide" and "polypeptide" are used interchangeably herein to denote a polymer of at least two amino acids covalently linked by an amide bond, regardless of length or post-translational modification (e.g., glycosylation or phosphorylation). A protein, peptide or polypeptide can comprise any suitable L- and/or D-amino acid, for example, common a-amino acids (e.g., alanine, glycine, valine), non-a-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "*Protecting Groups in Organic Synthesis*," John Wiley and Sons, 1991. The functional groups of a protein, peptide or polypeptide can also be derivatized (e.g., alkylated) or labeled (e.g., with a detectable label, such as a fluorogen or a hapten) using methods known in the art. A protein, peptide or polypeptide can comprise one or more modifications (e.g., amino acid linkers, acylation, acetylation, amidation, methylation, terminal modifiers (e.g., cyclizing modifications), N-methyl-α-amino group substitution), if desired. In addition, a protein, peptide or polypeptide can be an analog of a known and/or naturally-occurring peptide, for example, a peptide analog having conservative amino acid residue substitution(s).

As used herein, the term "sequence identity," refers to the extent to which two nucleotide sequences, or two amino acid sequences, have the same residues at the same positions when the sequences are aligned to achieve a maximal level of identity, expressed as a percentage. For sequence alignment and comparison, typically one sequence is designated as a reference sequence, to which a test sequences are compared. The sequence identity between reference and test sequences is expressed as the percentage of positions across the entire length of the reference sequence where the reference and test sequences share the same nucleotide or amino acid upon alignment of the reference and test sequences to achieve a maximal level of identity. As an example, two sequences are considered to have 70% sequence identity when, upon alignment to achieve a maximal level of identity, the test sequence has the same nucleotide or amino acid residue at 70% of the same positions over the entire length of the reference sequence.

Alignment of sequences for comparison to achieve maximal levels of identity can be readily performed by a person of ordinary skill in the art using an appropriate alignment method or algorithm. In some instances, the alignment can include introduced gaps to provide for the maximal level of identity. Examples include the local homology algorithm of Smith & Waterman, *Adv. Appl. Math.* 2:482 (1981), the homology alignment algorithm of Needleman & Wunsch, *J. Mol. Biol.* 48:443 (1970), the search for similarity method of Pearson & Lipman, *Proc. Nat'l. Acad. Sci. USA* 85:2444 (1988), computerized implementations of these algorithms (GAP, BESTFIT, FASTA, and TFASTA in the Wisconsin Genetics Software Package, Genetics Computer Group, 575 Science Dr., Madison, Wis.), and visual inspection (see generally Ausubel et al., Current Protocols in Molecular Biology).

When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters. A commonly used tool for determining percent sequence identity is Protein Basic Local Alignment Search Tool (BLASTP) available through National Center for Biotechnology Information, National Library of Medicine, of the United States National Institutes of Health. (Altschul et al., 1990).

Genetically Modified Aerobic Bacterium

In one aspect, the present invention provides a genetically modified aerobic bacterium comprising a polynucleotide encoding an electrically conductive fusion protein that comprises a non-native (e.g., *Geobacter*) pilin monomer.

The term "non-native pilin monomer" refers to a pilin monomer from a different species of bacteria. In some embodiments, the non-native pilin monomer is from a species of anaerobic bacteria. In some embodiments, the non-native pilin monomer is from *Geobacter.*

The term "fusion protein" refers to a recombinant single protein molecule. A fusion protein can comprise all or a portion of two or more different proteins and/or peptides that are attached by covalent bonds (e.g., peptide bonds).

Genetically modified aerobic bacteria of the invention can be used to produce the fusion proteins described herein recombinantly, using routine methods and reagents that are well known in the art. See, e.g., Current Protocols in Molecular Biology, Second Edition, Ausubel et al. eds., John Wiley & Sons, 1992; and Molecular Cloning: a Laboratory Manual, 2nd edition, Sambrook et al., 1989, Cold Spring Harbor Laboratory Press. For example, a polynucleotide encoding a fusion protein can be introduced and expressed in an aerobic bacterium (e.g., an *Escherichia coli* (*E. coli*) cell) described herein, and the expressed fusion protein can be isolated/purified from the aerobic bacterium (e.g., in inclusion bodies) using routine methods and readily available reagents. For example, DNA fragments coding for different protein sequences (e.g., a signal sequence or a peptide tag, etc.) can be ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., Current Protocols in Molecular Biology, 1992).

In some embodiments, the genetically modified aerobic bacterium is non-pathogenic. In some embodiments, the genetically modified aerobic bacterium is *E. coli, Shewanella oneidensis, Myxococcus xanthus, Bacillus subtilis, Caulobacter crescentus, Thermus* thermophiles or *Sulfolobus acidocaldarius* (archaeon), or a combination thereof.

In some embodiments, the genetically modified aerobic bacterium is an *E. coli* cell. In some embodiments, the genetically modified aerobic bacterium is a ΔfimA *E. coli* cell. In some embodiments, the genetically modified aerobic bacterium is a ΔfimA, ΔfliC *E. coli* cell.

In some embodiments, the genetically modified aerobic bacterium further comprises a polynucleotide encoding a pilus assembly protein (e.g., an *E. coli* pilus assembly protein) or a variant thereof. In some embodiments, the pilus assembly protein is a wildtype pilus assembly protein. In some embodiments, the pilus assembly protein is a variant of the wildtype pilus assembly protein. In some embodiments, the variant of the pilus assembly protein has at least 80% amino acid sequence identity to the wildtype pilus assembly protein. For example, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or about 99%, amino acid sequence identity to the wildtype pilus assembly protein.

In some embodiments, the pilus assembly protein is a wildtype *E. coli* pilus assembly protein. In some embodiments, the variant of the pilus assembly protein has at least 90% amino acid sequence identity to the wildtype *E. coli* pilus assembly protein. In some embodiments, the pilus assembly protein is hofB, hofC, hofM, hofN, hofO, hovP, hofQ, ppdA, ppdB, ygdB, ppdC or gspO, or a combination thereof. In some embodiments, the pilus assembly protein comprises hofB, hofC, hofM, hofN, hofO, hovP, hofQ, ppdA, ppdB, ygdB, ppdC and gspO.

In some embodiments, the pilus assembly protein is a wildtype *Myxococcus xanthus* pilus assembly protein. In some embodiments, the variant of the pilus assembly protein has at least 90% amino acid sequence identity to the wildtype *Myxococcus xanthus* pilus assembly protein. In some embodiments, the pilus assembly protein is PilB, PilC, PilM, PilN, PilO, PilP, PilQ, TsaP, PilX1, PilV1, PilV2, PilV3, PilW1, PilW2, PilW3, FimU1, FimU2 or FimU3, or a combination thereof. In some embodiments, the pilus assembly protein is PilB, PilC, PilM, PilN, PilO, PilP, PilQ, TsaP, PilX1, PilV1, PilV2, PilV3, PilW1, PilW2, PilW3, FimU1, FimU2 and FimU3.

In some embodiments, the genetically modified aerobic bacterium comprises an artificial operon composed of a cluster of two or more polynucleotides encoding pilus assembly proteins. In some embodiments, the artificial operon is a lac operon, a L-arabinose operon or a tetracycline operon. In some embodiments, the artificial operon is the lac operon.

In some embodiments, the artificial operon (e.g., lac operon) comprises hofB-hofC-hofM-hofN-hofO-hovP-hofQ-ppdA-ppdB-ygdB-ppdC-gspO. In some embodiments, the artificial operon comprises a variant of hofB-hofC-hofM-hofN-hofO-hovP-hofQ-ppdA-ppdB-ygdB-ppdC-gspO.

In some embodiments, the artificial operon (e.g., lac operon) comprises pilB-pilC-pilM-pilN-pilO-pilP-pilQ-tsaP-pilX1-pilV1-pilV2-pilV3-pilW1-pilW2-pilW3-fimU1-fimU2-fimU3. In some embodiments, the artificial operon comprises a variant of pilB-pilC-pilM-pilN-pilO-pilP-pilQ-tsaP-pilX1-pilV1-pilV2-pilV3-pilW1-pilW2-pilW3-fimU1-fimU2-fimU3.

In some embodiments, the polynucleotide encoding the pilus assembly protein or a variant thereof comprises a ribosome binding site selected from the group consisting of SEQ ID NOs:1-9 (Table 1) and combinations thereof. In some embodiments, the ribosome binding site is selected from SEQ ID NOs:1-3, 5, 7, 9 and combinations thereof. In some embodiments, the ribosome binding site of hofB is set forth in SEQ ID NOs:5. In some embodiments, the ribosome binding site of hofM is set forth in SEQ ID NOs:7. In some embodiments, the ribosome binding site of ppdA is set forth in SEQ ID NO:9.

In some embodiments, the polynucleotide encoding the pilus assembly protein or a variant thereof comprises a polynucleotide sequence selected from the group consisting of SEQ ID NOs:10-15 and combinations thereof. In some embodiments, the polynucleotide encoding the pilus assembly protein or a variant thereof comprises a polynucleotide sequence selected from the group consisting of SEQ ID NOs:11, 13, 15 and combinations thereof. In some embodiments, the sequence between hofC and hofM is set forth in SEQ ID NO:11. In some embodiments, the sequence between hofQ and ppdA is set forth in SEQ ID NO: 13. In some embodiments, the sequence between ppdC and gspO is set forth in SEQ ID NO: 15.

In some embodiments, the polynucleotide encoding the pilus assembly protein or a variant thereof is codon optimized.

In some embodiments, the polynucleotide encoding the pilus assembly protein is operably linked to an expression control polynucleotide sequence. In some embodiments, the expression control polynucleotide sequence comprises a promoter. Non-limiting examples of promoters include T7 promoter, T5 promoter, Sigma 54 promoter, Sigma 70 promoter, Sigma 32 promoter, PBAD promoter, etc., or a variant thereof (including synthetic). In some embodiments, the expression control polynucleotide sequence comprises a strong *E. coli* promoter. In some embodiments, the strong *E. coli* promoter is the tac promoter.

In some embodiments, the expression control polynucleotide sequence comprises a binding site for the lac repressor, the AraC repressor or the TetR repressor, or a combination thereof. In some embodiments, the expression control polynucleotide sequence comprises a binding site for the lac repressor. In some embodiments, the expression control polynucleotide sequence comprises a binding site for the AraC repressor. In some embodiments, the expression control polynucleotide sequence comprises a binding site for the TetR repressor.

In some embodiments, the polynucleotide encoding the pilus assembly protein or variant thereof is integrated into the chromosome of the bacterium.

In some embodiments, the polynucleotide encoding the pilus assembly protein is located on an extrachromosomal plasmid in the bacterium.

In some embodiments, the polynucleotide encoding the electrically conductive fusion protein is integrated into the chromosome of the bacterium.

In some embodiments, the polynucleotide encoding the electrically conductive fusion protein is located on an extrachromosomal plasmid in the bacterium.

In some embodiments, the non-native pilin monomer is a *Geobacter* pilin monomer.

The term "*Geobacter* pilin monomer" refers to a pilin monomer produced by a *Geobacter* species, for example, a *Geobacter sulfurreducens* pilin monomer.

In some embodiments, the non-native pilin monomer is a *Calditerrivibrio nitroreducens* pilin monomer, a *Desulfurivibrio alkaliphilus* pilin monomer, a *Desulfatibacillum alkenivorans* pilin monomer, a *Desulfuromonas* sp. TF pilin monomer, a *Desulfuromonas thiophila* pilin monomer, a *Felxistipes sinusarabici* pilin monomer, a *Geoalkalibacter ferrihydriticus* pilin monomer, a *Geoalkalibacter subterraneu* pilin monomer, a *Geobacter bemidjiensis* pilin monomer, a *Geobacter bremensis* pilin monomer, a *Geobacter argillaceus* pilin monomer, a *Geobacter lovleyi* pilin monomer, a *Geobacter metallireducens* pilin monomer, a *Geobacter pickeringii* pilin monomer, a *Geopsychrobacter electrodiphilus* pilin monomer, a *Geobacter soli* pilin monomer, a *Geobacter* sp. OR-1 pilin monomer, a *Geobacter sulfurreducens* pilin monomer, a *Methanospirillum hungatei* pilin monomer, a *Smithella* sp. F21 pilin monomer, a *Geobacter* sp. M18 pilin monomer, a *Geobacter* sp. M21 pilin monomer, a *Pelobacter propionicus* pilin monomer, a *Pelobacter seleniigenes* pilin monomer, a *Smithella* Sp. F21 pilin monomer, a *Syntrophorhabdus aromaticivorans* pilin monomer, a *Syntrophobacter fumaroxidans* pilin monomer, a *Syntrophobacter* sp. SbD1 pilin monomer, a *Syntrophobacter* sp. DG 60 pilin monomer, a *Syntrophaceticus schinkii* pilin monomer, a *Syntrophus aciditrophicus* pilin monomer, a *Syntro-*

*phus gentianae* pilin monomer, a *Syntrophomonas zehnderi* pilin monomer, a *Tepidanaerobacter acetatoxydans* pilin monomer, a *Thermacetogenium phaeum* pilin monomer, or a combination thereof. In some embodiments, the non-native pilin monomer is a *Geobacter sulfurreducens* pilin monomer.

Non-limiting examples of pilin monomer sequences can be found, for example, in PCT/US2020/023824 (e.g., in Tables 1 and 2 of PCT/US2020/023824), incorporated by reference.

In some embodiments, the pilin monomer (e.g., *Geobacter* pilin monomer) is a type IV pilin monomer or a variant thereof. In some embodiments, the type IV pilin monomer is selected from the group consisting of PilA, PilE, GspG, EspG, OxpG, NE1308, SO0854, PulG, HofG, Yts1G, and combinations thereof.

In some embodiments, the *Geobacter* pilin monomer is a *Geobacter sulfurreducens* PilA monomer or a variant thereof. In some embodiments, the *Geobacter* pilin monomer comprises the amino acid sequence of wildtype *Geobacter sulfurreducens* PilA monomer (SEQ ID NO:16). In some embodiments, the *Geobacter* pilin monomer comprises an amino acid sequence that has at least 80% sequence identity to the wildtype *Geobacter sulfurreducens* PilA monomer (SEQ ID NO:16). For example, For example, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or about 99%, sequence identity to the wildtype *Geobacter sulfurreducens* PilA monomer (SEQ ID NO:16).

In some embodiments, the variant of the wildtype *Geobacter sulfurreducens* PilA monomer is a N-terminal truncation lacking from 1-5 (e.g., 1, 2, 3, 4, or 5) amino acids at the N-terminus of the wildtype *Geobacter sulfurreducens* PilA (SEQ ID NO:16). In some embodiments, the variant is a C-terminal truncation lacking from 1-5 (e.g., 1, 2, 3, 4, or 5) amino acids at the C-terminus of the wildtype *Geobacter sulfurreducens* PilA (SEQ ID NO:16). In some embodiments, the variant is a N-terminal addition having from 1-5 (e.g., 1, 2, 3, 4, or 5) additional amino acids at the N-terminus of the wildtype *Geobacter sulfurreducens* PilA (SEQ ID NO:16).

In some embodiments, the variant of the wildtype *Geobacter sulfurreducens* PilA monomer comprises an addition of an aromatic amino acid to the wildtype *Geobacter sulfurreducens* PilA (SEQ ID NO:16). In some embodiments, about 1-10 aromatic amino acids are added to SEQ ID NO:16. The number of aromatic amino acids added in SEQ ID NO:16 may be 1, 2, 3, 4, 5, 6, 7, 8, 9 or 10 amino acids; at least 1, 2, 3, 4, 5, 6, 7, 8 or 9 amino acids; or about 1-8, about 2-8, about 2-6, about 3-6 or about 4-6 amino acids.

In some embodiments, the variant of the wildtype *Geobacter sulfurreducens* PilA monomer comprises a deletion of one or more aromatic amino acids in the wildtype *Geobacter sulfurreducens* PilA (SEQ ID NO:16). In some embodiments, about 1-10 aromatic amino acids are deleted from SEQ ID NO:16. The number of aromatic amino acids deleted in SEQ ID NO:16 may be 1, 2, 3, 4, 5, 6, 7, 8, 9 or 10 amino acids; at least 1, 2, 3, 4, 5, 6, 7, 8 or 9 amino acids; or about 1-8, about 2-8, about 2-6, about 3-6 or about 4-6 amino acids.

In some embodiments, the variant of the wildtype *Geobacter sulfurreducens* PilA monomer comprises a substitution of an aromatic amino acid. In some embodiments, about 1-10 aromatic amino acids are substituted in SEQ ID NO:16. The number of aromatic amino acids substituted in SEQ ID NO:16 may be 1, 2, 3, 4, 5, 6, 7, 8, 9 or 10 amino acids; at least 1, 2, 3, 4, 5, 6, 7, 8 or 9 amino acids; or about 1-8, about 2-8, about 2-6, about 3-6 or about 4-6 amino acids. In some embodiments, the aromatic amino acid is substituted with a non-aromatic amino acid (e.g., alanine (A)). In some embodiments, the aromatic amino acid is substituted with a different aromatic amino acid (e.g., phenylalanine (F)-to-tryptophan (W) or tyrosine (Y)-to-W).

In some embodiments, the deleted or substituted aromatic amino acid is F24, F51, Y27, Y32, Y57, or a combination thereof in SEQ ID NO:16. In some embodiments, the substitution is F24A, F51A, Y27A, Y32A, Y57A, or a combination thereof in SEQ ID NO:16. In some embodiments, the substitution is F24W, F51W, Y27W, Y32W, Y57W, or a combination thereof in SEQ ID NO:16.

In some embodiments, the variant of the wildtype *Geobacter sulfurreducens* PilA monomer comprises a substitution of a non-aromatic amino acid with an aromatic amino acid. In some embodiments, about 1-10 non-aromatic amino acids are substituted in SEQ ID NO:16. The number of non-aromatic acids substituted in SEQ ID NO:16 may be 1, 2, 3, 4, 5, 6, 7, 8, 9 or 10 amino acids; at least 1, 2, 3, 4, 5, 6, 7, 8 or 9 amino acids; or about 1-8, about 2-8, about 2-6, about 3-6 or about 4-6 amino acids.

In some embodiments, the electrically conductive fusion protein is untagged.

In some embodiments, the electrically conductive fusion protein further comprises a peptide tag. In various embodiments, the fusion protein comprises a tag at the C-terminus of the *Geobacter* pilin monomer.

As used herein, the term "tag" refers to one or more amino acids that are covalently attached to a *Geobacter* pilin monomer (e.g., at the C-terminus of a *Geobacter sulfurreducens* PilA monomer or a variant thereof). In some embodiments, the tag is covalently attached to a *Geobacter* pilin monomer by a peptide bond.

In some embodiments, the tag is a single amino acid. In some embodiments, the single amino acid is cysteine.

In some embodiments, the peptide tag has a length of about (e.g., consists of) 2-200 amino acids, e.g., about 2-180, about 3-180, about 3-160, about 4-160, about 4-140, about 5-140, about 5-120, about 6-120, about 6-100, about 7-100, about 7-80, about 8-80, about 8-60, about 9-60, about 9-50, about 10-50, about 10-40, about 12-40, about 12-35, about 15-35, about 15-30, or about 20-30 amino acids. In some embodiments, the peptide tag consists of about 2-100 amino acids, e.g., about 2-90, about 3-90, about 3-80, about 4-80, about 4-70, about 5-70, about 5-60, about 6-60, about 6-50, about 7-50, about 7-40, about 8-40, about 8-30, about 9-30, about 9-20, or about 10-20 amino acids. In some embodiments, the peptide tag consists of about 2-50 amino acids. In some embodiments, the peptide tag consists of about 5-15 amino acids.

In some embodiments, the tag is a peptide. In some embodiments, the peptide tag comprises, consists of, or consists essentially of a polyhistidine sequence, for example, 2-10 consecutive histidine amino acids, e.g., a 2×His tag, 3×His tag, 4×His tag (SEQ ID NO:19), 5×His tag (SEQ ID NO:20), 6×His (SEQ ID NO:21), 7×His tag (SEQ ID NO:22), 8×His tag (SEQ ID NO:23), 9×His tag (SEQ ID NO:24), or 10×His tag (SEQ ID NO:25). In some embodiments, the peptide tag comprises, consists of, or consists essentially of a 6×His tag (SEQ ID NO:21).

In some embodiments, the peptide tag comprises, consists of, or consists essentially of HHHHHHC (SEQ ID NO:26).

In some embodiments, the peptide tag comprises, consists of, or consists essentially of a human influenza hemagglutinin (HA) sequence (SEQ ID NO:27).

In some embodiments, the peptide tag comprises or consists of a binding motif. Non-limiting examples of the binding motif include nucleic acid (e.g., DNA or RNA)-binding sequences, protein-binding sequences (e.g., an epitope tag or calmodulin binding protein (CBP)), and chemical-binding sequences, etc. Non-limiting examples of epitope tags include HA, FLAG, AU1, AUS, Myc, Glu-Glu, OLLAS, T7, V5, VSV-G, E-Tag, S-Tag, Avi, HSV, KT3, and TK15, etc. Non-limiting examples of chemical-binding sequences include 6His, beta-galactosidase, Strep-tag, Strep-tag II, maltose binding protein, glutathione S transferase (GST), etc. Additional non-limiting examples of tags can be found in PCT/US2020/023824 (e.g., in Table 3 of PCT/US2020/023824), incorporated by reference.

In some embodiments, the electrically conductive fusion protein further comprises a signal sequence. In some embodiments, the signal sequence is at the N-terminus of the *Geobacter* pilin monomer. In some embodiments, the signal sequence comprises MDKQRG (SEQ ID NO:17). In some embodiments, the electrically conductive fusion protein comprises an amino acid sequence set forth in SEQ ID NO:18.

While example embodiments have been particularly shown and described, it will be understood by those skilled in the art that various changes in form and details may be made therein without departing from the scope of the embodiments encompassed by the appended claims.

Polynucleotides

In another aspect, the present invention provides a polynucleotide encoding a pilus assembly protein (e.g., an *E. coli* pilus assembly protein) or a variant thereof. In some embodiments, the pilus assembly protein is a wildtype pilus assembly protein. In some embodiments, the pilus assembly protein is a variant of the wildtype pilus assembly protein. In some embodiments, the variant of the pilus assembly protein has at least 80% sequence identity to the wildtype pilus assembly protein. For example, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or about 99%, sequence identity to the wildtype pilus assembly protein.

In some embodiments, the pilus assembly protein is a wildtype *E. coli* pilus assembly protein. In some embodiments, the variant of the pilus assembly protein has at least 80% sequence identity to the wildtype *E. coli* pilus assembly protein. For example, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or about 99%, sequence identity to the wildtype *E. coli* pilus assembly protein.

In some embodiments, the pilus assembly protein is hofB, hofC, hofM, hofN, hofO, hovP, hofQ, ppdA, ppdB, ygdB, ppdC or gspO, or a combination thereof. In some embodiments, the pilus assembly protein comprises hofB, hofC, hofM, hofN, hofO, hovP, hofQ, ppdA, ppdB, ygdB, ppdC and gspO.

In some embodiments, the polynucleotide comprises an artificial operon composed of a cluster of two or more polynucleotides encoding pilus assembly proteins. In some embodiments, the artificial operon is the lac operon.

In some embodiments, the artificial operon comprises hofB-hofC-hofM-hofN-hofO-hovP-hofQ-ppdA-ppdB-ygdB-ppdC-gspO. In some embodiments, the artificial operon comprises a variant of hofB-hofC-hofM-hofN-hofO-hovP-hofQ-ppdA-ppdB-ygdB-ppdC-gspO. In some embodiments, the variant of hofB-hofC-hofM-hofN-hofO-hovP-hofQ-ppdA-ppdB-ygdB-ppdC-gspO has at least 70% sequence identity to the wildtype pilus assembly protein. For example, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or about 99%, sequence identity to the wildtype pilus assembly protein.

In some embodiments, the artificial operon comprises a sequence encoding a pilus assembly protein or a variant thereof, wherein the pilus assembly protein is hofB, hofC, hofM, hofN, hofO, hovP, hofQ, ppdA, ppdB, ygdB, ppdC or gspO, or a combination thereof.

In some embodiments, the polynucleotide comprises a ribosome binding site selected from the group consisting of SEQ ID NOs:1-9 (Table 1) and combinations thereof. In some embodiments, the ribosome binding site is selected from SEQ ID NOs:1-3, 5, 7, 9 and combinations thereof. In some embodiments, the ribosome binding site of hofB is set forth in SEQ ID NOs:5. In some embodiments, the ribosome binding site of hofM is set forth in SEQ ID NOs:7. In some embodiments, the ribosome binding site of ppdA is set forth in SEQ ID NOs:9.

In some embodiments, the polynucleotide comprises a sequence selected from the group consisting of SEQ ID NOs:10-15 and combinations thereof. In some embodiments, the polynucleotide comprises a sequence selected from the group consisting of SEQ ID NOs:11, 13, 15 and combinations thereof.

In some embodiments, the polynucleotide further comprises an expression control polynucleotide sequence operably linked to the polynucleotide, a polynucleotide sequence encoding a selectable marker, or both. In some embodiments, the expression control polynucleotide sequence comprises a promoter sequence, an enhancer sequence, or both. In some embodiments, the expression control polynucleotide sequence comprises an inducible promoter sequence. In some embodiments, transcription of the fusion protein can be regulated by an inducer. In some embodiments, the inducer is Isopropyl 3-D-1-thiogalactopyranoside (IPTG).

In some embodiments, the polynucleotide is operably linked to an expression control polynucleotide sequence. In some embodiments, the expression control polynucleotide sequence comprises a strong *E. coli* promoter. In some embodiments, the strong *E. coli* promoter is the tac promoter.

The term "promoter" refers to a region of DNA to which RNA polymerase binds and initiates the transcription of a gene.

The term "operably linked" means that the nucleic acid is positioned in the recombinant polynucleotide, e.g., vector, in such a way that enables expression of the nucleic acid under control of the element (e.g., promoter) to which it is linked.

The term "selectable marker element" is an element that confers a trait suitable for artificial selection. Selectable marker elements can be negative or positive selection markers.

Methods of Producing Electrically Conductive Protein Nanowires

In another aspect, the present invention provides a method of producing electrically conductive protein nanowires, comprising the steps of:

a) introducing a polynucleotide into a genetically modified aerobic bacterium, wherein the polynucleotide encodes an electrically conductive fusion protein that comprises a non-native pilin monomer;
b) placing the bacterium in a culture medium conditioned for producing the pili;
c) culturing the bacterium for a time sufficient to produce a desired quantity of the pili; and
d) isolating the pili from the culture medium, thereby producing the electrically conductive protein nanowires.

In another aspect, the present invention provides a method of producing electrically conductive protein nanowires, comprising the steps of:

a) placing a genetically modified aerobic bacterium in a culture medium conditioned for producing the pili, wherein the bacterium comprises a polynucleotide encoding an electrically conductive fusion protein that comprises a non-native pilin monomer;
b) culturing the bacterium for a time sufficient to produce a desired quantity of the pili; and
c) isolating the pili from the culture medium, thereby producing the electrically conductive protein nanowires.

The genetically modified aerobic bacterium and the polynucleotide employed in the method are as described herein.

In some embodiments, the culture medium is M9 medium. In some embodiments, the host cell is cultured at about 30° C. In some embodiments, the method further comprises culturing the host cell in the presence of an inducing molecule. In some embodiments, the inducing molecule is Isopropyl P-D-1-thiogalactopyranoside (IPTG).

In some embodiments, isolating the pili from the culture medium comprises:

a) harvesting the bacterium;
b) pelleting the bacterium (e.g. by centrifuging at 4,000 rpm at 4° C. for a sufficient amount of time (e.g., about 15 min);
c) resuspending the bacterium in ethanolamine buffer (e.g., pH 10.5, 150 mM and a sufficient volume (e.g., 30 mL));
d) shearing the pili from the cells (e.g., blended in a Waring blender on low speed for a sufficient amount of time (e.g., 2 min);
e) removing the cells (e.g., by centrifuging at 5,000 g at 4° C. for a sufficient amount of time (e.g., 30 min);
f) solubilizing remaining cellular debris (e.g., using about 6 mM Triton X-100); or
g) filtering the culture medium, or a combination thereof.

In some embodiments, isolating the pili from the culture medium comprises filtering the culture medium. In some embodiments, filtering uses a filter having a molecular weight cutoff of about 90 kDa to about 110 kDa. For example, about: 90 kDa, 95 kDa, 100 kDa, 105 kDa or 110 kDa, or 90-105 kDa, 90-100 kDa, 90-95 kDa, 95-110 kDa, 95-105 kDa, 95-100 kDa, 100-110 kDa, 100-105 kDa or 100-105 kDa.

In some embodiments, filtering uses a membrane filter made from poly ether sulfone.

In another aspect, the present invention provides a method of harvesting protein nanowires from a host cell (e.g., an *E. coli* cell) culture medium, comprising filtering the culture medium a filter having a molecular weight cutoff of about 90 kDa to about 110 kDa. For example, about: 90 kDa, 95 kDa, 100 kDa, 105 kDa or 110 kDa, or 90-105 kDa, 90-100 kDa, 90-95 kDa, 95-110 kDa, 95-105 kDa, 95-100 kDa, 100-110 kDa, 100-105 kDa or 100-105 kDa. In some embodiments, filtering uses a membrane filter made from poly ether sulfone.

In another aspect, the present invention provides electrically conductive protein nanowires produced using the method described herein.

EXAMPLES

In vivo assembly of protein nanowires with microorganisms has several advantages over in vitro synthesis. Advantages include much lower cost and greater flexibility in wire design options in a platform driven with inexpensive, renewable feedstocks. A diversity of bacteria and archaea assemble peptides that show homology to bacterial type IV pilins into electrically conductive protein nanowires (Reguera et al., 2005; Tan et al., 2017; Walker et al., 2018a; Walker et al., 2019; Walker et al., 2018b), but the protein nanowires of *Geobacter sulfurreducens* have been most intensively investigated (Lovley, 2017b; Lovley and Walker, 2019). *G. sulfurreducens* protein nanowires can be fabricated in vitro with inexpensive acetate as the feedstock. Once the cells are grown, the protein nanowires can be harvested, retaining their conductive properties (Adhikari et al., 2016; Malvankar et al., 2011; Tan et al., 2016a; Tan et al., 2017).

The exquisite machinery that bacteria possess to assemble pilin proteins into filaments (Hospenthal et al., 2017) confers great control over protein nanowire production, yielding a highly uniform product. The microbial assembly process also offers substantial opportunities for producing diverse, new types of protein nanowires. For example, the conductivity of protein nanowires produced with *G. sulfurreducens* has been tuned over a million folds with simple modifications to the *G. sulfurreducens* pilin gene to either increase or decrease the abundance of aromatic amino acids (Lovley, 2017b; Lovley and Walker, 2019). Pilin genes can be designed to encode additional peptides at the carboxyl end of the pilin, yielding protein nanowires that retain their conductivity and display the added peptides on the outer surface of the wires (Ueki et al., 2019). This peptide display along the wires offers substantial possibilities for introducing peptide ligands to confer specific sensing functions to protein nanowire devices with a flexibility in sensor design not feasible with other materials such as carbon nanotubes or silicon nanowires (Ueki et al., 2019). Peptides might also be designed to promote binding of protein nanowires to surfaces to facilitate wire alignment or as chemical linkers with polymers for the fabrication of composite materials (Ueki et al., 2019). Synthetic gene circuits introduced to control the expression of multiple pilin monomer genes within a single cell offer the possibility to further tune protein nanowire function by producing heterogeneous wires comprised of multiple types of pilin monomers with the stoichiometry of each types precisely controlled (Ueki et al., 2019). These design options would be difficult to replicate in with in vitro assembly of protein nanowires or fabrication of nanowires from non-biological materials.

*Geobacter*-fabricated protein nanowires have several other advantages over traditional non-biological nanowire materials. Production of the protein nanowires requires 100-fold less energy than is required for fabricating silicon nanowires or carbon nanotubes (Lovley, 2017a). No toxic chemicals are required for protein nanowire fabrication and the final product is biocompatible, environmentally benign, and recyclable (Lovley, 2017a). Yet, protein nanowires are remarkably robust, maintaining function even under harsh CMOS-compatible fabrication conditions (Sun et al., 2018). Proof-of-concept studies have demonstrated the dynamic sensing response of *Geobacter*-fabricated protein nanowires; their ability to function as the conductive component in flexible electronics; and a remarkable ability to harvest energy from natural air humidity in the form of electricity (Adhikari et al., 2016; Liu et al., 2019a; Sun et al., 2018; Ueki et al., 2019).

Barriers to large-scale production have been a limitation to realizing the potential of *Geobacter* protein nanowires for possible applications. *G. sulfurreducens* must be grown anaerobically to produce protein nanowires. This requirement adds technical complexity and costs. A strain of *Pseudomonas aeruginosa*, grown aerobically, heterologously expressed the *G. sulfurreducens* pilin gene with the assembly of conductive protein nanowires with properties similar to the protein wires expressed in *G. sulfurreducens* (Liu et al., 2019b). However, *P. aeruginosa* is a pathogenic microorganism and not thus not ideal for large-scale commercial production of protein nanowires. Furthermore, the expression of the protein nanowires in *P. aeruginosa* remained under the control of the native regulatory system, limiting options for controlling the timing and extent of nanowire expression (Liu et al., 2019b).

It is hypothesized that *Escherichia coli* may be an ideal chassis for protein nanowire fabrication. *E. coli* is a common platform for the commercial scale production of organic commodities. The substantial *E. coli* genetic toolbox, including the possibility of introducing unnatural amino acids, could provide broad options for designing protein nanowires. Non-pathogenic strains of *E. coli* typically do not express type IV pili. However, Rico et al. (Rico et al., 2019) developed an artificial operon of pilus assembly protein genes from pathogenic *E. coli* that, when introduced in to non-pathogenic *E. coli*, yielded a strain that expressed the same type IV pili that pathogenic *E. coli* express (Rico et al., 2019). This finding, and the fact that bacteria sometimes assemble heterologous pilins into pili (Liu et al., 2014; Liu et al., 2019b; Tan et al., 2016b; Tan et al., 2017; Vargas et al., 2013; Walker et al., 2018a), suggested that it may be possible to develop a non-pathogenic strain of *E. coli* that would express electrically conductive *Geobacter* protein nanowires.

Another limitation to large-scale in vivo production of protein nanowires has been the methods for separating the protein nanowires from cells. Previously described methods have included multiple laborious steps, often with strategies such as ultracentrifugation and/or salt precipitation procedures that would be difficult to economically scale (Malvankar et al., 2011; Tan et al., 2017).

Described herein is the construction of a strain of *E. coli* amended with genes for the expression of type IV pili and the *G. sulfurreducens* pilin gene. This strain produces electrically conductive protein nanowires with characteristics similar to the protein nanowires expressed by *G. sulfurreducens*. Simple aerobic growth of the *E. coli* designed for protein nanowire production, coupled with a newly developed, simplified method for harvesting protein nanowires from cells, indicate that large-scale production of electrically conductive protein nanowires is feasible.

Example 1. Materials and Methods

*E. coli* Strain and Culture Conditions

*E. coli* NEB 10-beta (New England Biolabs, Ipswich, Mass.) was grown at 37° C. in LB medium supplemented with appropriate antibiotics as necessary for plasmid preparation, as previously described (Miller, 1972) The strain of *E. coli* used for the production of protein nanowires has the potential to make other filaments such as fimbrae (Type I pili) and flagella. To prevent the expression of these filaments, genes necessary for their expression were deleted. The gene for FimA, the primary monomer for type I pili, was deleted as previously described (Datsenko and Wanner, 2000; Baba et al., 2006) to construct *E. coli* ΔfimA (kanamycin-sensitive). The strains expressing the modified *E. coli* pilin or the synthetic peptide for assembly into e-PNs were built in this strain. Further, the gene for FliC, the flagellin of flagella, was deleted as previously described (Datsenko and Wanner, 2000; Baba et al., 2006) from the *E. coli* ΔfimA strain to construct *E. coli* ΔfimA ΔfliC strain.

Construction of the Expression Vector for Type IV Pilus Assembly

An expression vector for type IV pilus assembly was constructed as described previously (Rico et al., 2019) with several modifications (FIGS. 1A-1D). To construct the basic expression vector for type IV pilus assembly, the T7 promoter in the plasmid vector pET24b (Novagen) was replaced with the tac promoter (de Boer, 1983). The DNA fragment containing the tac promoter and lac operator was amplified by PCR with the primer pair Ptac-F/Olac-R (Table 3) and pCD341 (Dehio et al., 1998) as the template. The PCR product was digested with BglII and XbaI and replaced the BglII-XbaI region containing T7 promoter and lac operator in pET24b. The resultant plasmid was designated p24Ptac.

Next, genes for *E. coli* type IV pilus assembly without the major pilin gene were cloned in p24Ptac. The genes include hofB (ATPase), hofC (platform protein), hofM (assembly protein), hofN (assembly protein), hofO (assembly protein), hofP (assembly protein), hofQ (secretin), ppdA (minor pilin), ppdB (minor pilin), ygdB (minor pilin), ppdC (minor pilin), and gspO (prepilin peptidase) (Rico et al., 2019). The DNA fragment containing ppdA, ppdB, ygdB, ppdC, and gspO was prepared by two-step PCR. Fragments containing ppdA, ppdB, ygdB, and ppdC or gspO were amplified by PCR with primer pairs, ppdA-F/ppdC-R and gspO-F/gspO-R (Table 3), respectively. The fragment containing ppdA, ppdB, ygdB, ppdC, and gspO was amplified by PCR with these PCR products as the template and the primer pair ppdA-F/gspO-R. The PCR product was digested with HindIII and XhoI and cloned in pBluescript II SK (Stratagene, San Diego, Calif.). The fragment containing hofM, hofN, hofO, hofP, and hofQ was amplified by PCR with the primer pair hofM-F/hofQ-R (Table 3). The PCR product was digested with XbaI and HindIII and cloned in the plasmid containing ppdA, ppdB, ygdB, ppdC, and gspO. The fragment containing hofB and hofC was amplified by PCR with the primer pair hofB-F/hofC-R (Table 3). The PCR product was digested with SacI and XbaI and cloned in the plasmid containing hofM, hofN, hofO, hofP, hofQ, ppdA, ppdB, ygdB, ppdC, and gspO. The fragment containing hofB, hofC, hofM, hofN, hofO, hofP, hofQ, ppdA, ppdB, ygdB, ppdC, and gspO was prepared by digesting the plasmid containing hofB, hofC, hofM, hofN, hofO, hofP, hofQ, ppdA, ppdB, ygdB, ppdC, and gspO with SacI and XhoI and cloned in p24Ptac (FIG. 1). The resultant plasmid was designated T4PAS/p24Ptac.

Expression and Harvesting of Pili Composed of the *E. coli* Pilin PpdD

The fragment containing a gene for PpdD with the HA tag (FIG. 1E) was amplified with the primer pair ppdD-F/ppdD-HA-R (Table 3), digested with NdeI and SacI, and cloned in T4PAS/p24Ptac. The resultant plasmid was termed ppdD-HA/T4PAS/p24Ptac.

For initial studies with the *E. coli* strain expressing the *E. coli* pilin PpdD, the plasmids ppdD-HA/T4PAS/p24Ptac or T4PAS/p24Ptac were transformed into *E. coli* ΔfimA. A single colony from an LB agar plate containing kanamycin (Miller, 1972) was inoculated in TB medium (Novagen) supplemented with 1% glycerol and kanamycin and incubated at 30° C. for 24 h to the stationary phase. Pili were sheared from the cells and precipitated with TCA as described previously (Rico et al., 2019).

Previous studies with protein nanowires expressed with the microbe *Geobacter sulfurreducens* demonstrated that the applications of protein nanowires can be expanded by adding peptides to the carboxyl end of the pilin monomer gene (Ueki et al., 2019). The added peptides were displayed on the outer surface of the protein nanowires when *G. sulfurreducens* assembled the pilin monomers into the nanowires (Ueki et al., 2019). The displayed peptides can serve as ligands for binding analytes of interest when protein nanowires are incorporated into electronic sensing devices or could enhance the incorporation of the protein nanowires into nanowire-polymer composites, or facilitate nanowire binding to cells or abiotic surfaces (Ueki et al., 2019).

To determine if it was possible to functionalize protein nanowires expressed in *E. coli* in a similar manner, a synthetic pilin gene was designed to incorporate a His-tag at the carboxyl end of the pilin. The amino acid sequence of PilA-6His monomer of ePN-6His (SEQ ID NO:43) is shown in Table 2. The DNA sequence of PilA-6His monomer of ePN-6His is shown below.

```
                                    (SEQ ID NO: 42)
ATGGACAAGCAACGCGGTTTCACCCTTATCGAGCTGCTGA

TCGTCGTTGCGATCATCGGTATTCTCGCTGCAATTGCGAT

TCCGCAGTTCTCGGCGTATCGTGTCAAGGCGTACAACAGC

GCGGCGTCAAGCGACTTGAGAAACCTGAAGACTGCTCTTG

AGTCCGCATTTGCTGATGATCAAACCTATCCGCCCGAAAG

TCACCACCACCACCACCACTAA.
```

Expression and Harvesting of e-PNs

A fragment encoding a gene for a synthetic pilin monomer, which was similar to the PilA monomer of *G. sulfurreducens* but included the signal sequence of PpdD instead of the original PilA signal sequence (FIG. 1F), was amplified with the primer pair EPS-GspilA-F/GspilA-R (Table 3). The amplified fragment was digested with NdeI and SacI and cloned in T4PAS/p24Ptac. The resultant plasmid, designated GspilA/T4PAS/p24Ptac, was transformed into *E. coli* ΔfimA. The resultant strain, designated *E. coli* strain GPN (*Geobacter*protein nanowires) was grown on 10 cm diameter culture plates of standard LB medium (Miller, 1972) amended with kanamycin and solidified with agar. After overnight growth at 30° C., cells were scraped from the surface and suspended in 6 mL of M9 medium (Miller, 1972). Twenty plates of M9 medium supplemented with 0.5% glycerol, 0.5 mM IPTG, and kanamycin were spread-plated with 300 μL of the suspended cells. The plates were incubated at 30° C. for 48 h. The cells were harvested from the plates with 1 mL of M9 medium (500 μL to scrape, 500 μL to wash) for each plate. The 20-mL suspension of cell scrapings was centrifuged at 4000 rpm for 15 min at 4° C. to pellet the cells. The supernatant was discarded, and the cells were resuspended in 30 mL of 150 mM ethanolamine buffer (pH 10.5) and poured into a Waring blender. The tubes were washed three times with 20 mL of the ethanolamine buffer, which was also added to the blender. The 90-mL suspension was blended for 2 min on low speed to shear the e-PNs from the cells. The contents of the blender were transferred to a centrifuge bottle along with a wash of the blender with 10 mL of ethanolamine buffer. The blended material was centrifuged at 5000 g for 30 min at 4° C. to remove the cells. The supernatant containing the e-PNs was collected. Triton X-100 detergent was added at a final concentration of 6 mM to solubilize any remaining cellular debris. The mixture was shaken at 100 rpm at room temperature for 45 min and then added to a stirring filtration unit that had a 100 kDa molecular weight cutoff membrane filter made from poly(ether sulfone) (Omega membrane 100 K 76 mm, Pall Corporation, Port Washington, N.Y.) to collect the e-PNs on the filter. Additional ethanolamine buffer was added to dilute the sample to yield a final Triton X-100 concentration of 2 mM. The sample was filtered under nitrogen gas (69 kPa). The sample on the filter was washed four times with 100 mL of water. The e-PNs were collected from the filter by scraping the surface into 500 μL of water. The scraping procedure was repeated two more times to yield a suspension of e-PNs in 1.5 mL of water.

Western Blot Analysis

The presence of pilin monomers in whole-cell extracts and pili preparations was evaluated with Western blot analysis. Whole-cell extracts were prepared with B-PER Complete Bacterial Protein Extraction Reagent (Thermo Fisher Scientific, Waltham, Mass.). Western blot analysis was conducted as described previously (Ueki et al., 2019). PpdD-HA pilin was detected with an anti-HA antibody (HA Tag Polyclonal Antibody, Invitrogen). The *G. sulfurreducens* pilin monomer, PilA, was detected with an anti-PilA antibody (Ueki et al., 2019).

Protein Nanowire Conductance

Figure 6A:
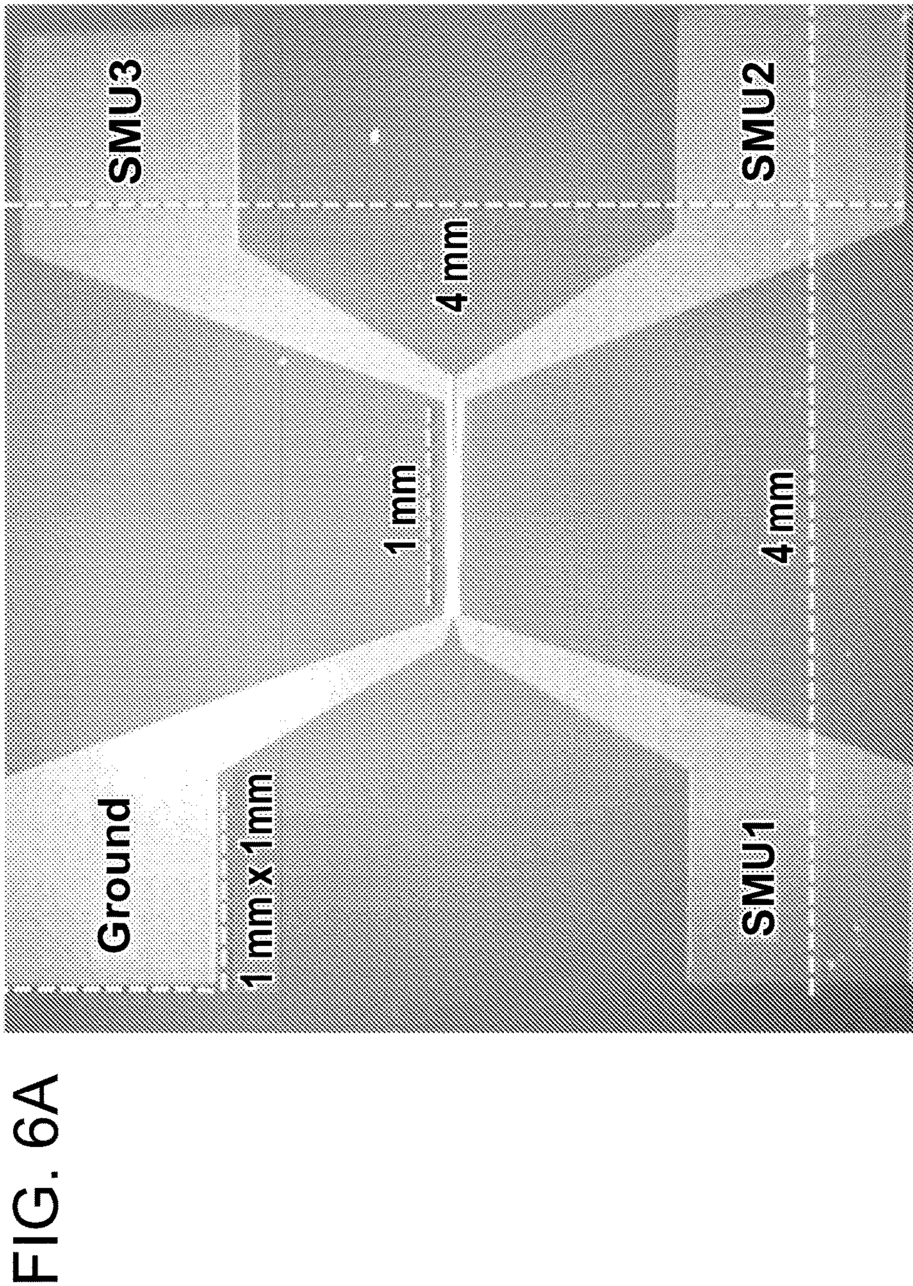
FIGS. 6A and 6B show the architecture of the nanoelectrode devices used on the 4-probe measurements. The electrodes were made using photolithography with a custom mask. The wafer is composed of a 300-nm oxide layer on which 10 nm of tungsten then 40 nm of gold were placed on for the electrodes. The source voltage is applied at SMU1 and is removed at Ground. The voltage difference is measured between SMU2 and SMU3.
Figure 6B:
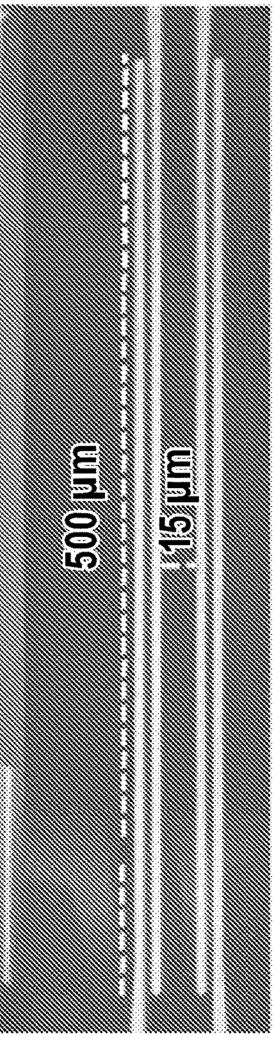

The conductance of e-PNs expressed in *E. coli* from the *G. sulfurreducens* pilin was analyzed as previously described (Walker et al., 2018a; Walker et al., 2019). For four-probe measurements of thin-film conductance, the e-PN preparation in water was adjusted to 500 μg of protein/μL. As previously described (Walker et al., 2018a), a 2-μL aliquot of the e-PN preparation was drop-cast onto the center of three different gold electrode nanoarrays (FIG. 6) and allowed to dry for 1 h at 24° C., after which another 2 μL was drop-cast and left to dry overnight at 24° C. Each of the three electrode nanoarrays was analyzed with a Keithley 4200 semiconductor characterization system set up with four probes to conduct a current-voltage (I-V) curve using a $\pm 30\times10^{-8}$ V sweep with a 5-second delay and a 250-second hold time. The voltage was injected at the source and removed at ground, and the current between the two inner electrodes was measured (FIG. 6). The analysis of each of the three nanoarrays was repeated in triplicate. Thin-film conductance was calculated by extracting the slope of the linear fit of the current-voltage response for each of the three measurements on the three electrodes using the formula G=I/V, where G is the conductance, I is the current, and V is the voltage.

In order to evaluate the conductance of individual e-PNs, a 100 μL aliquot of a culture of *E. coli* expressing the *G.*

*sulfurreducens* pilin was drop-cast onto highly oriented pyrolytic graphite and allowed to sit for 10 min. Then the excess liquid was wicked away with a Kimwipe, and an equal volume of deionized water was added to wash off excess salts, etc. The sample was blotted dry and then dried for 12 h at 24° C. The prepared samples were loaded into an Oxford Instruments Cypher ES Environmental AFM and equilibrated for at least 2 h. The AFM was operated in ORCA electrical mode with a Pt/Ir-coated Arrow-ContPT tip with a force constant of 0.2 N/m (NanoWorld AG, Neuchatel, Switzerland). e-PNs were identified in amplitude mapping mode (AM-AFM). Point-mode current-voltage spectroscopy was carried out by switching to contact mode and gently touching the conductive tip, which acted as a translatable top electrode, to the top of the e-PN with a force of 1 nN. A voltage sweep of 0.6 V set at 0.99 Hz was applied to three independent points on each of three individual e-PNs. The conductance was calculated, as above, from the slope of the linear fit of the current-voltage response between −0.2 and 0.2 V.

Example 2. Genetically Modifying a Strain of *E. coli*

A non-pathogenic strain of *E. coli* was genetically modified for expressing synthetic electrically conductive fusion proteins that comprise a *Geobacter* pilin monomer.

The gene fimA was deleted to prevent the formation of type I pili using previously described genetic methods.

It was determined that a gene for a pilin of interest can be cloned separately from the genes for the *E. coli* type IV pilus assembly machinery (see, e.g., FIG. 1A). A gene for the LacI repressor was included in the expression vector (EMD Chemicals, Gibbstown, N.J. (Novagen)) to repress the genes when they are preferred not to be expressed (e.g., during cloning and preculture).

Figure 1B:
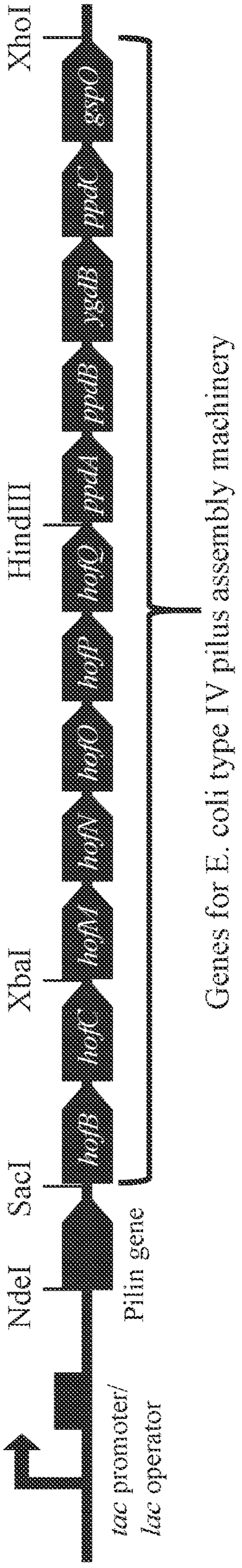

Restriction enzymes, different from those previously used, were used to connect the gene clusters (see, e.g., FIG. 1). The tac promoter, one of the strongest promoters in *E. coli*, was used to enhance transcription of the genes for the assembly of the type IV pili (FIG. 1B).

Ribosome binding sites for hofB, hofM, and ppdA were modified to improve translation efficiency (see, e.g., FIG. 1C).

A gene cluster containing ppdA, ppdB, ygdB, and ppdC and gspO was generated by performing two PCR steps, instead of using a restriction enzyme. Unnecessary sequences within the intergenic regions were deleted (see, e.g., FIG. 1D).

Example 3. Expressing Pili in *E. coli*

The *E. coli* pilin gene, ppdD, was modified to code for the HA tag, YPYDVPDYA (SEQ ID NO:27), at the C-terminal end (PpdD-HA) for evaluation of modification of pili and detection of PpdD-HA with a commercially available antibody.

Figure 2A:
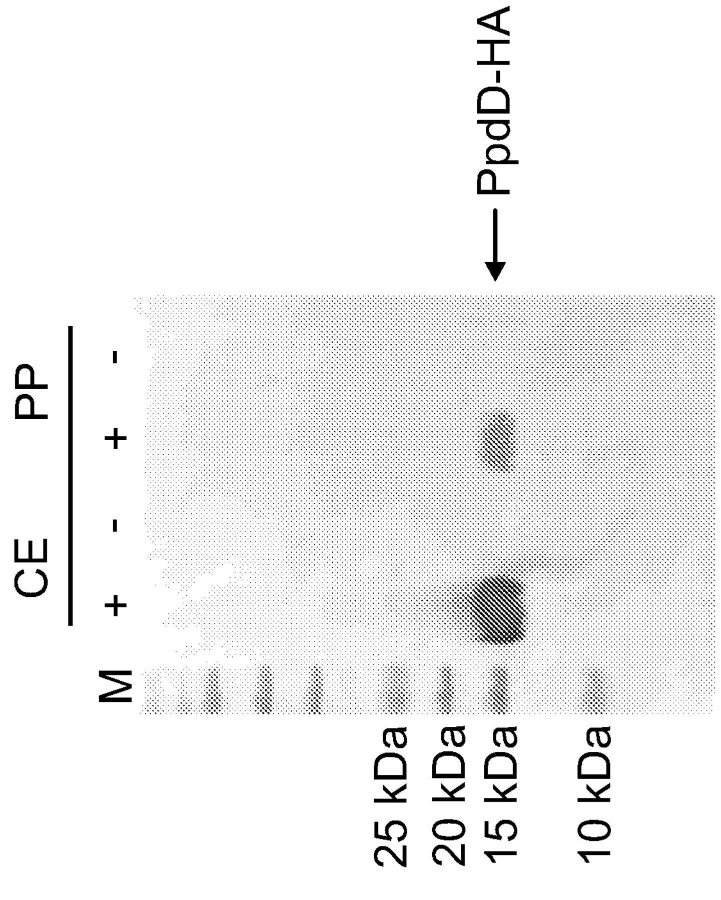
FIGS. 2A and 2B show expression of modified pili in *E. coli* strain GPN, which contains genes for pilus assembly and the gene for a synthetic pilin monomer designed to yield electrically conductive protein nanowires (e-PNs).

A strain containing the genes for PpdD-HA pilus assembly was grown in TB medium (EMD Chemicals, Gibbstown, N.J. (Novagen)) supplemented with glycerol and kanamycin. Expression of PpdD-HA monomer was detected by Western blot analysis with the commercially available anti-HA antibody (FIG. 2A). PpdD-HA was detected in the cell extract from the strain containing the genes for PpdD-HA pilus assembly but not in extracts from a control strain that lacked the gene for PpdD-HA (FIG. 2A).

PpdD-HA pili were sheared from cells with vortexing. The sheared pili were precipitated with ammonium sulfate. PpdD-HA was detected in the sheared fraction from the strain containing the genes for PpdD-HA pilus assembly but not from the control strain without the PpdD-HA gene (FIG. 2A). These results confirmed that the modified expression system for type IV pilus assembly was effective for pili production.

Example 4. Expressing and Harvesting Electrically Conductive Protein Nanowires in *E. coli*

Figure 2B:
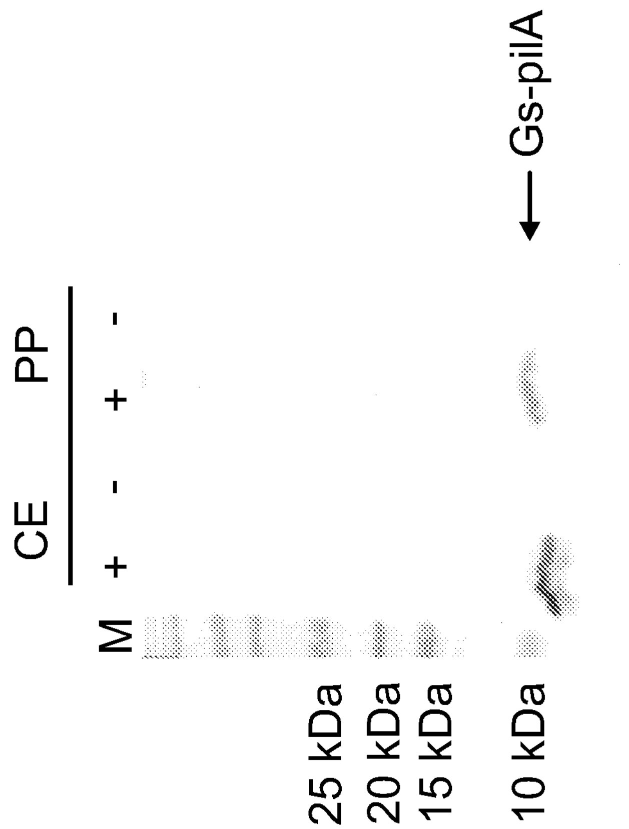

A gene was designed to be expressed in *E. coli* to yield a synthetic peptide monomer for assembly into electrically conductive protein nanowires (e-PNs). The peptide was similar to the *G. sulfurreducens* pilin monomer, PilA, with the exception that the signal sequence was replaced with the *E. coli* PpdD signal sequence to facilitate electrically conductive protein nanowire assembly in *E. coli* (FIG. 1F). The gene for the synthetic e-PN monomer was cloned into the location designated "pilin gene" (FIG. 1A). The strain with the synthetic gene for the e-PN monomer was designated *E. coli* strain GPN (*Geobacter*protein nanowire). The e-PN monomer was detected in whole-cell extracts of strain GPN with PilA antibody but not in the control strain that lacked the gene for the e-PN monomer (FIG. 2B).

e-PNs were harvested from strain GPN with physical shearing from the cells, as in previous studies of e-PNs expressed in *G. sulfurreducens* (Malvankar et al., 2011). In those previous studies, the cells were separated from the sheared e-PNs by centrifugation, and then the e-PNs in the supernatant were collected with ultracentrifugation or ammonium sulfate precipitation (Malvankar et al., 2011). These methods of e-PN collection were labor-intensive and would be difficult to adapt to large-scale production. Therefore, the e-PN supernatant preparation was treated with Triton X-100 detergent to solubilize any remaining cell debris, and then the e-PNs were collected on a filter with a 100 kDa molecular weight cutoff. This method is simpler and faster than previously described e-PN purification methods.

Figure 5A:
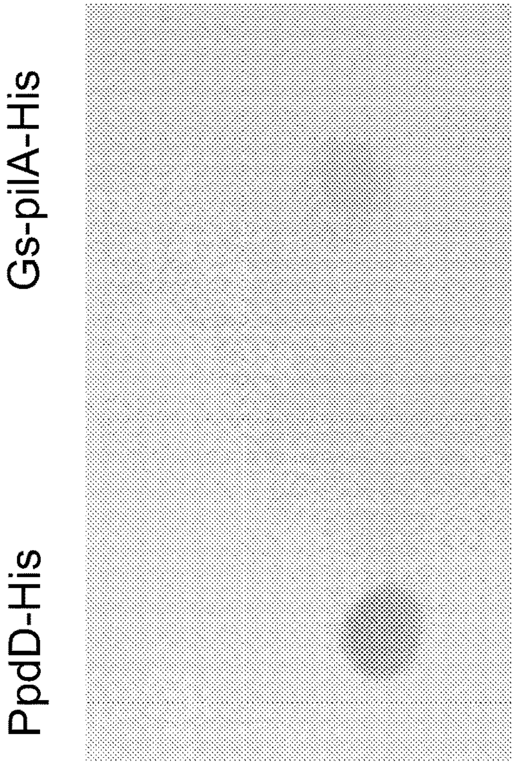
FIGS. 5A-5C show expression of e-PNs with a His-tag at the C-terminus end in *E. coli* strain GPN.
Figure 5B:
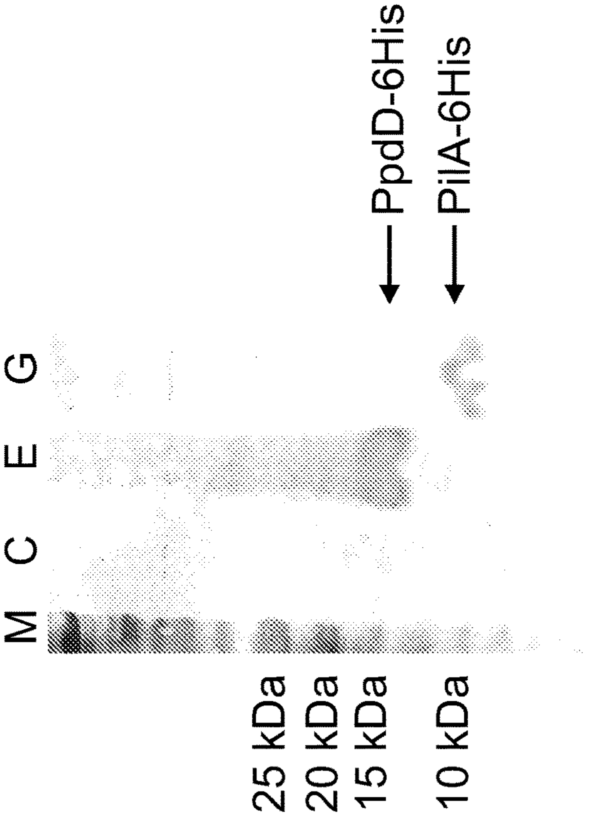
Figure 5C:
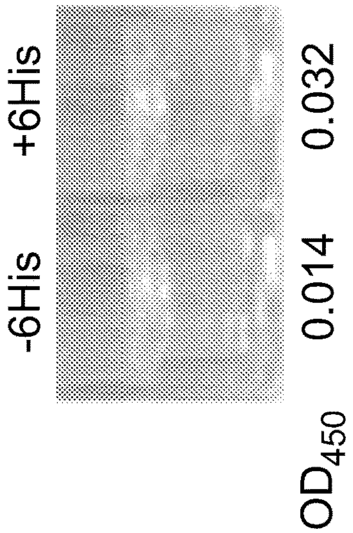

To determine if it was possible to functionalize protein nanowires expressed in *E. coli* in a similar manner, a synthetic pilin gene was designed to incorporate a His-tag at the carboxyl end of the pilin. Expression of the pilin monomer with the His-tag was verified using a Western dot blot (FIG. 5A) or with immunogold labeling of cell lysates (FIG. 5B, Lane G). Histidine is known to bind metals. The nickel-binding capability of protein nanowires assembled from the His-Tag pilin was compared to protein nanowires comprised of pilin without the His-Tag with a Ni-HRP (horseradish peroxidase) ELISA (enzyme-linked immunosorbent assay) conducted in microplates. Optical density at 450 nm is indicative of the amount of nickel bound. The results demonstrated increased nickel binding by the protein nanowires displaying the His-Tag (FIG. 5C). These results demonstrate the potential to express a diversity of modified pilins in *E. coli* that can be assembled into protein nanowires with different functionalities.

Example 5. Characterizing the e-PNs Expressed in *E. coli* Strain GPN

Figure 3A:
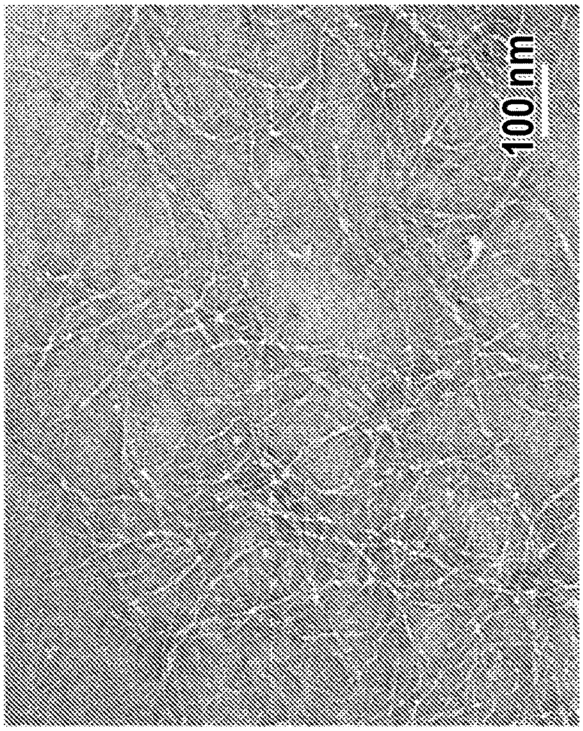
FIGS. 3A and 3B depict characterization of the e-PNs expressed in *E. coli* strain GPN.

The e-PNs harvested from *E. coli* strain GPN were ca. 3 nm in diameter and several micrometers in length (FIG. 3A), a morphology similar to the e-PNs expressed in G. *sulfurreducens*. No filaments were observed in similar preparations when the gene for the e-PN monomer was omitted from *E. coli* strain GPN. Denaturation of the e-PNs from *E. coli* strain GPN yielded a monomer that reacted with PilA antibody, whereas the monomer was not detected in preparations from the control strain without the gene for the e-PN monomer (FIG. 3B).

Figure 3B:
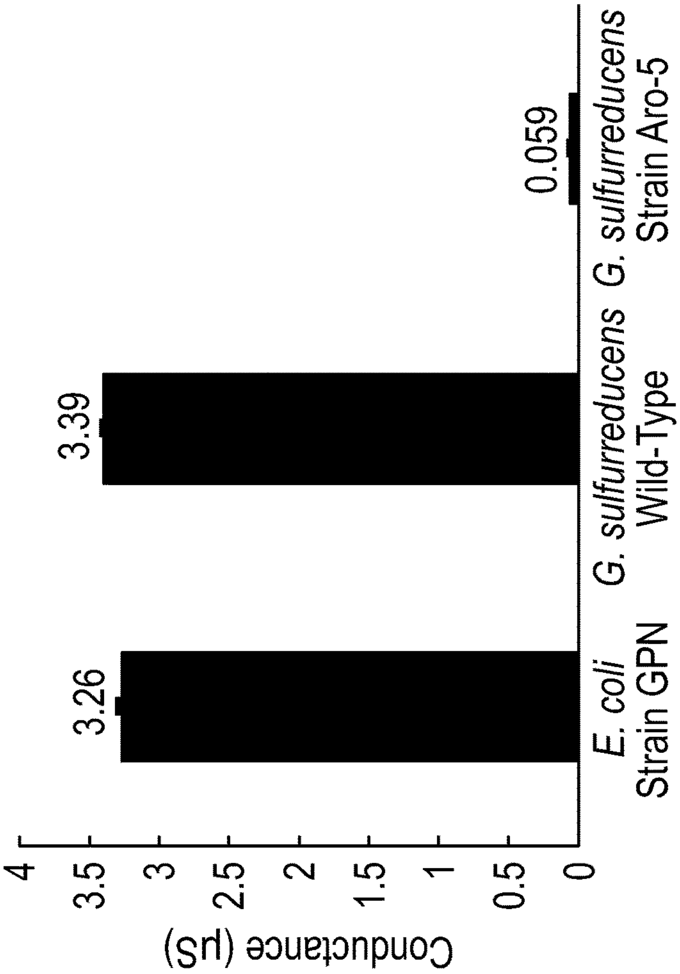

The conductance of thin films of the e-PNs from *E. coli* strain GPN, determined with a nanoelectrode array as previously described (Walker et al., 2018a) was 3.26±0.35 S, similar to the conductance of 3.39±0.04 S for e-PNs harvested from *G. sulfurreducens* (FIG. 3B). The conductance of these e-PNs was much higher than the conductance of wires harvested from the Aro-5 strain of *G. sulfurreducens* (FIG. 3B), which expresses a synthetic pilin gene designed to yield protein nanowires with low conductivity (Vargas et al., 2013; Adhikari et al., 2016)

Figure 4A:
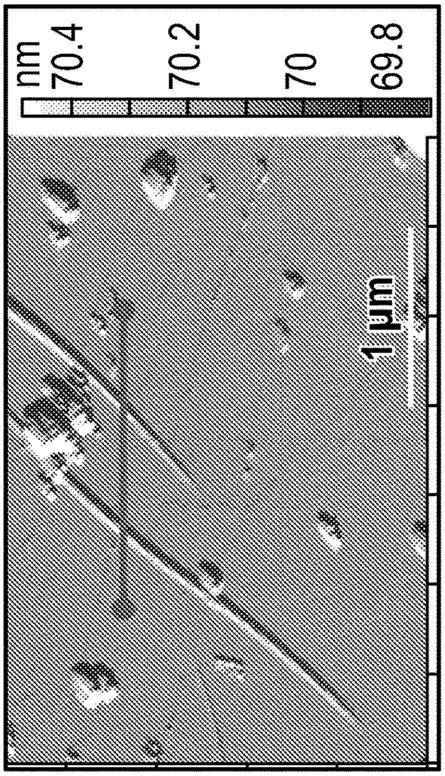
FIGS. 4A-4D characterizes individual e-PNs expressed in *E. coli* strain GPN.
Figure 4B:
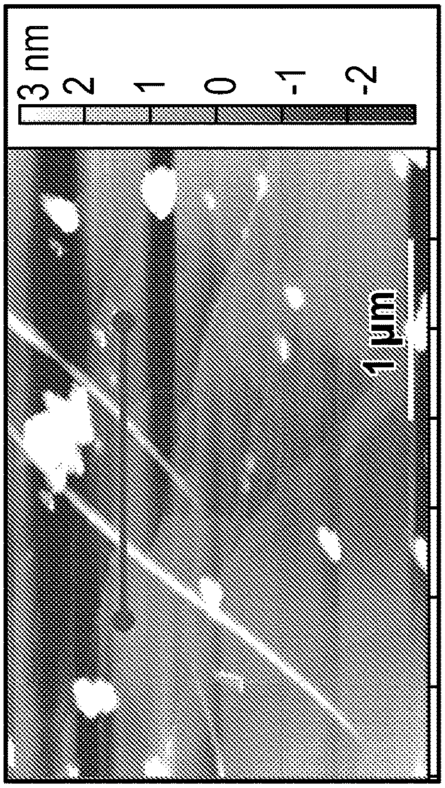
Figure 4C:
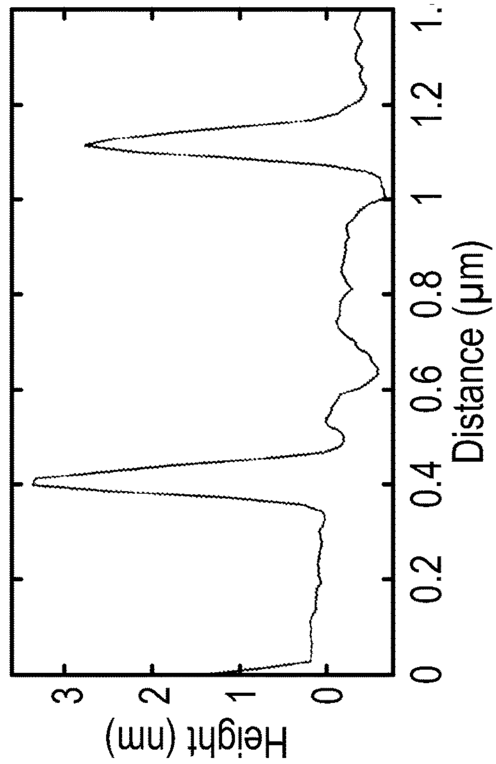
Figure 4D:
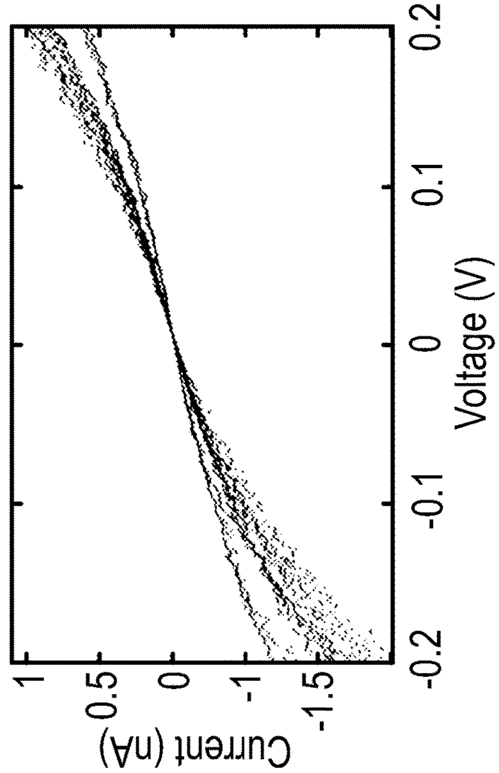

The conductance of individual e-PNs was evaluated on highly oriented pyrolytic graphite with atomic force microscopy employing a conductive tip, as previously described (Walker et al., 2019) The diameter of the e-PNs was 3.00±0.04 nm (n=18; six measurements on three independent pili), the same as e-PNs expressed with G. *sulfurreducens* (FIGS. 4A-4C). The e-PNs were conductive with an Ohmic-like current-voltage response (FIG. 4D). The conductance of the individual e-PNs, 4.3±0.8 nS (n=9), compared well with the previously reported (Walker et al., 2019) conductance of 4.5±0.3 nS for individual e-PNs expressed in *G. sulfurreducens*.

The protein nanowires expressed in this strain of *E. coli*, which contained the gene for the synthetic protein nanowire monomer and *E. coli* genes for the type IV pilus assembly machinery strain of *E. coli*, were characterized. In order to generate substantial biomass, the *E. coli* strain was grown on culture plates of standard LB medium, amended with kanamycin, and solidified with agar. After overnight growth at 30° C., cells were scraped from the surface and suspended in 6 ml of M9 media. Twenty plates of M9 medium were spread-plated with 300 μl of the suspended cells. The plates were incubated at 30° C. for 48 hours. Cells were harvested from the plates with 1 ml of M9 media (500 μl to scrape, 500 μl to wash) for each plate. The 20-ml suspension of cell scrapings was centrifuged at 4000 rpm for 15 minutes at 4° C. to pellet the cells. The supernatant was discarded, and the cells were resuspended in 30 ml of 150 mM ethanolamine (pH 10.5) buffer and poured into a blender. The tubes were washed three times with 20 ml of the ethanolamine buffer, which was also added to the blender. The 90-ml suspension was blended for 2 minutes on low speed. The contents of the blender were transferred to a centrifuge bottle along with a wash of the blender with 10 ml of ethanolamine buffer. The blended material was centrifuged at 5000×g for 30 minutes at 4° C. The supernatant was collected.

Previous studies have collected *G. sulfurreducens* protein nanowires with ultracentrifugation or ammonium sulfate precipitation. These collection methods are labor intensive and will be difficult to adapt to large-scale production. In our method, the protein nanowires sheared from strain GPN and separated from Triton X100 detergent was added to provide a final concentration of 6 mM. The mixture was shaken at 100 rpm at room temperature for 45 minutes then added to a stirring filtration unit that had a 100 kDa molecular weight cutoff membrane filter made from polyethersulfone. Additional —ethanolamine buffer was added to dilute the sample to yield a final Triton X100 concentration of 2 mM. The sample was filtered under nitrogen gas (10 psi). The sample on the filter was washed four times with 100 ml of water. The protein nanowires were collected from the filter by scrapping the surface into 500 μl of water. The scrapping procedure was repeated two more times to yield a suspension of protein nanowires in 1.5 ml of water.

The fabrication of e-PNs with *E. coli* described herein has substantial advantages over expression in *G. sulfurreducens*. Special equipment and expertise are required to anaerobically culture *G. sulfurreducens*, whereas *E. coli* can be simply grown under ambient aerobic atmospheric conditions. Thus, when coupled with the finding that the e-PNs can be collected with a simple filtration method, expression of e-PNs in *E. coli* is more suited for large-scale e-PN production.

Furthermore, e-PN expression in *E. coli* enables much greater flexibility for the design of a wider diversity of e-PNs than would currently be possible with *G. sulfurreducens*. Tools for the genetic manipulation of *G. sulfurreducens* are limited, and only the simplest synthetic gene circuits have been adapted for this organism (Ueki et al., 2016). The much broader range of strategies for introducing genes and controlling their expression in *E. coli* (Choi et al., 2016; Pontrelli et al., 2018) may facilitate the design and expression of e-PNs with unique properties and functionalities that could not readily be fabricated with *G. sulfurreducens*.

TABLE 1

Polynucleotide Sequences

| SEQ ID NO: | Polynucleotides | Sequences |
|---|---|---|
| 1 | ribosome binding site (RBS) | AGGAGGNNNNNNNATG |
| 2 | | AGGAGGNNNNNNNNATG |
| 3 | | AGGAGGNNNNNNNNNATG |
| 4 | WT hofB RBS | ACTAAGGAGCGGCAATG |
| 5 | modified hofB RBS | AGGAAGGAGCGGCAATG |
| 6 | WT hofM RBS | ATATACCCGTCAGAGTG |
| 7 | modified hofM RBS | AGAAGGCCGTCAGAGTG |
| 8 | WTppdARBS | TCCATACTGCCGGCATG |
| 9 | modified ppdA RBS | AGGAGACTGCCGGCATG |
| 10 | original sequence between hofC & hofM | CCATGGAAGGCAAGCCAGACGCATTGATATACCCGTCAGA |
| 11 | modified sequence between hofC & hofM | TCTAGAAGGCCGTCAGA |
| 12 | original sequence between hofQ & ppdA | GGCGCGCCTTCTCCTCGCTCCATACTGCCGGC |
| 13 | modified sequence between hofQ & ppdA | AAGCTTAGGAGACTGCCGGC |
| 14 | original sequence between ppdC & gspO | CTCGAGGTCCTTCAGGGAGCAACAATA |
| 15 | modified sequence between ppdC & gspO | CAGGGAGCAACAATA |

TABLE 2

| Polypeptide Sequences | | |
|---|---|---|
| SEQ ID NO: | Polypeptides | Sequences |
| 16 | WT *Geobacter sulfurreducens* PilA | FTLIELLIVVAIIGILAAIAIPQFSAYRVKAYNSAASSDLRNLKTALESAFADDQTYPPES |
| 17 | *E. coli* signal sequence | MDKQRG |
| 18 | modified *Geobacter sulfurreducens* PilA | MDKQRGFTLIELLIVVAIIGILAAIAIPQFSAYRVKAYNSAASSDLRNLKTALESAFADDQTYPPES |
| 43 | | MDKQRGFTLIELLIVVAIIGILAAIAIPQFSAYRVKAYNSAASSDLRNLKTALESAFADDQTYPPESHHHHHH |
| 19 | Histidine (His) Tag | HHHH |
| 20 | | HHHHH |
| 21 | | HHHHHH |
| 22 | | HHHHHHH |
| 23 | | HHHHHHHH |
| 24 | | HHHHHHHHH |
| 25 | | HHHHHHHHHH |
| 26 | | HHHHHHC |
| 27 | HA Tag | YPYDVPDYA |

TABLE 3

| Primers | | | |
|---|---|---|---|
| SEQ ID NO: | Name | Sequence | Enzyme |
| 28 | Ptac-F | TTCAGATCTGCAAATATTCTGAAATGAGC | BglII |
| 29 | Olac-R | TTCTCTAGAGGGGAATTGTTATCCGCTCAC | XbaI |
| 30 | hofB-F | TCTGAGCTCAGGAAGGAGCGGCAATGAATATTC | SacI |
| 31 | hofC-R | ATCTCTAGATTATCCCATCCCACTCATC | XbaI |
| 32 | hofM-F | ATCTCTAGAAGGCCGTCAGAGTGACGGGTGATAAG | XbaI |
| 33 | hofQ-R | TCTAAGCTTACTCACTGGAAACCAGTC | HindIII |
| 34 | ppdA-F | TCTAAGCTTAGGAGACTGCCGGCATGAAAACACAAC | HindIII |
| 35 | ppdC-R | GTCATTATTGTTGCTCCCTGCTACTGACGATTCGGACAATG | |

TABLE 3-continued

| Primers | | | |
|---|---|---|---|
| SEQ ID NO: | Name | Sequence | Enzyme |
| 36 | gspO-F | CATTGTCCGAATCGTCAGTAGCAGGGAGCAACAATAATGAC | |
| 37 | gspO-R | TCTCTCGAGTTATCTGCAAGCACAGATCC | XhoI |
| 38 | ppdD-F | TCTCATATGGACAAGCAACGCGGTTTTAC | NdeI |
| 39 | ppdD-HA-R | TCTGAGCTCTTACGCGTAGTCCGGCACGTCGTACGGGTAGTTGGCGTCATCAAAGCGG | SacI |
| 40 | EPS-GspilA-F | TCTCATATGGACAAGCAACGCGGTTTCACCCTTATCGAGCTGC | NdeI |
| 41 | GspilA-R | TCTGAGCTCTTAACTTTCGGGCGGATAGG | SacI |

REFERENCES

1. Adhikari, R. Y., N. S. Malvankar, M. T. Tuominen, and D. R. Lovley. 2016. Conductivity of individual *Geobacter* pili. RSC Advances. 6:8354-8357.
2. Baba, T., Ara, T., Hasegawa, M., Takai, Y., Okumura, Y., Baba, M., Datsenko, K. A., Tomita, M., Wanner, B. L., and Mori, H. 2006. Construction of *Escherichia coli* K-12 in-frame, single-gene knockout mutants: the Keio collection. Mol. Syst. Biol. 2, 2006.
3. Chang Y. W., Rettberg L. A., Treuner-Lange A., Iwasa J., Søgaard-Andersen L. and Jensen G. J. 2016. Architecture of the type IVa pilus machine. Science. 351(6278):1165.
4. Choi, K. R., Shin, J. H., Cho, J. S., Yang, D., and Lee, S. Y. 2016. Systems metabolic engineering of *Escherichia coli*. EcoSal Plus 7, 1-56.
5. Cuthbertson L. and Nodwell J. R. 2013. The TetR family of regulators. Microbiol Mol Biol Rev. 77(3):440-75.
6. Creasey, R. C. G., A. B. Mostert, T. A. H. Nguyen, B. Virdis, S. Freguia, and B. Laycock. 2018. Microbial nanowires-electron transport and the role of synthetic analogues Acta Biomater. 69:1-30.
7. Creasey, R. C. G., Y. Shingaya, and T. Nakayama. 2015. Improved electrical conductance through self-assembly of bioinspired peptides into nanoscale fibers. Materials Chemistry and Physics. 158:52-59.
8. Datsenko, K. A. and Wanner, B. L. 2000. One-step inactivation of chromosomal genes in *Escherichia coli* K-12 using PCR products. Proc. Natl. Acad. Sci. U.S.A 97, 6640-6645.
9. de Boer, H. A., Comstock, L. J., and Vasser, M. 1983. The tac promoter: a functional hybrid derived from the trp and lac promoters. Proc. Natl. Acad. Sci. U.S.A 80, 21-25.
10. Dehio, M., Knorre, A., Lanz, C., and Dehio, C. 1998. Construction of versatile high-level expression vectors for *Bartonella henselae* and the use of green fluorescent protein as a new expression marker. Gene 215, 223-229.
11. Gutermann, T., and E. Gazit. 2018. Toward peptide-based bioelectronics: reductionist design of conductive pili mimetics. Bioelctronics in Medicine. 1:131-137.

12. Hospenthal, M. K., T. R. D. Costa, and G. Waksman. 2017. A comprehensive guide to pilus biogenesis in Gram-negative bacteria. Nature Reviews Microbiology. 15:365-379.
13. Ing, N. L., M. Y. El-Naggar, and A. I. Hochbaum. 2018a. Going the distance: long-range conductivity in protein and peptide bioelectronic materials. J. Phys. Chem. B. 122:1043-10423.
14. Ing, N. L., R. K. Spencer, S. H. Luong, H. D. Nguyen, and A. I. Hochbaum. 2018b. Electronic conductivity in biomimetic α-helical peptide nanofibers and gels. ACS Nano. 12:2652-2661.
15. Liu, X., H. Gao, J. E. Ward, X. Liu, B. Yin, T. Fu, J. Chen, D. R. Lovley, and J. Yao. 2019a. Sustained electric power generation from ambient humidity using microbial protein nanowires. (in third round of review at Nature).
16. Liu, X., P. L. Tremblay, N. S. Malvankar, K. P. Nevin, D. R. Lovley, and M. Vargas. 2014. A *Geobacter sulfurreducens* strain expressing *Pseudomonas aeruginosa* type IV pili localizes OmcS on pili but Is deficient in Fe(III) oxide reduction and current production. Appl Environ Microbiol. 80:1219-1224.
17. Liu, X., S. Wang, A. Xu, L. Zhang, H. Liu, and L. Z. Ma. 2019b. Biological synthesis of high-conductive pili in aerobic bacterium *Pseudomonas aeruginosa*. Appl. Microbiol. Biotechnol. 103:1535-1544.
18. Lovley, D. R. 2017a. e-Biologics: Fabrication of sustainable electronics with 'green' biological materials. mBio. 8:e00695-00617.
19. Lovley, D. R. 2017b. Electrically conductive pili: biological function and potential applications in electronics. Curr. Opin. Electrochem. 4:190-198.
20. Lovley, D. R., and D. J. F. Walker. 2019. *Geobacter* protein nanowires. Frontiers in Microbiology. 10:2078.
21. Malvankar, N. S., M. Vargas, K. P. Nevin, A. E. Franks, C. Leang, B.-C. Kim, K. Inoue, T. Mester, S. F. Covalla, J. P. Johnson, V. M. Rotello, M. T. Tuominen, and D. R. Lovley. 2011. Tunable metallic-like conductivity in nanostructured biofilms comprised of microbial nanowires. Nature Nanotechnology. 6:573-579.
22. Miller, J. H. 1972. Experiments in Molecular Genetics, Cold Spring Harbor Laboratory Press, Cold Spring Harbor, N. Y.
23. Pontrelli, S., Chiu, T.-Y., Lan, E. I., Chen, F. Y.-H., Chang, P., and Liao, J. C. 2018. *Escherichia coli* as a host for metabolic engineering. Metab. Eng. 50, 16-46.
24. Reguera, G., K. D. McCarthy, T. Mehta, J. S. Nicoll, M. T. Tuominen, and D. R. Lovley. 2005. Extracellular electron transfer via microbial nanowires. Nature. 435: 1098-1101.
25. Rico, A. L., W. Zheng, N. Petiot, E. H. Egelman, and O. Francetic. 2019. Functional reconstitution of the type IVa pilus assembly system from enterohaemorrhagic *Escherichia coli*. Molecular Microbiology. 111:732-749.
26. Schleif R. 2003. AraC protein: a love-hate relationship. Bioessays. 25(3):274-82.
27. Smolskaya, S. and Andreev, Y. A. 2019. Site-specific incorporation of unnatural amino acids into *Escherichia coli* recombinant protein: methodology development and recent achievement. Biomolecules 9, 255.
28. Sun, Y. L., H. Y. Tang, A. Ribbe, V. Duzhko, T. L. Woodard, J. E. Ward, K. P. Nevin, S. Nonnenmann, T. P. Russell, T. Emrick, and D. R. Lovley. 2018. Conductive composite materials fabricated with microbially produced protein nanowires. Small. 14:1802624.
29. Tan, Y., R. Y. Adhikari, N. S. Malvankar, S. Pi, J. E. Ward, T. L. Woodard, K. P. Nevin, Q. Xia, M. T. Tuominen, and D. R. Lovley. 2016a. Synthetic biological protein nanowires with high conductivity. Small. 12:4481-4485.
30. Tan, Y., R. Y. Adhikari, N. S. Malvankar, J. E. Ward, K. P. Nevin, T. L. Woodard, J. A. Smith, O. L. Snoeyenbos-West, A. E. Franks, M. T. Tuominen, and D. R. Lovley. 2016b. The low conductivity of *Geobacter* uraniireducens pili suggests a diversity of extracellular electron transfer mechanisms in the genus *Geobacter*. Frontiers in Microbiology. 7:980.
31. Tan, Y., R. Y. Adhikari, N. S. Malvankar, J. E. Ward, T. L. Woodard, K. P. Nevin, and D. R. Lovley. 2017. Expressing the *Geobacter metallireducens* PilA in *Geobacter sulfurreducens* yields pili with exceptional conductivity. mBio. 8:e02203-02216.
32. Ueki, T., Nevin, K. P., Woodard, T. L., and Lovley, D. R. 2016. Genetic switches and related tools for controlling gene expression and electrical outputs of *Geobacter sulfurreducens*. J. Ind. Microbiol. Biotechnol. 43, 1561-1575.
33. Ueki, T., D. J. F. Walker, P.-L. Tremblay, K. P. Nevin, J. E. Ward, T. L. Woodard, S. S. Nonnenmann, and D. R. Lovley. 2019. Decorating the outer surface of microbially produced protein nanowires with peptides. ACS Synthetic Biology 8:1809-1817.
34. Vargas, M., N. S. Malvankar, P.-L. Tremblay, C. Leang, J. A. Smith, P. Patel, O. Snoeyenbos-West, K. P. Nevin, and D. R. Lovley. 2013. Aromatic amino acids required for pili conductivity and long-range extracellular electron transport in *Geobacter sulfurreducens* mBio. 4:e00105-00113.
35. Walker, D. J. F., R. Y. Adhikari, D. E. Holmes, J. E. Ward, T. L. Woodard, K. P. Nevin, and D. R. Lovley. 2018a. Electrically conductive pili from genes of phylogenetically diverse microorganisms. ISME J. 12:48-58.
36. Walker, D. J. F., E. Martz, D. E. Holmes, Z. Zhou, S. S. Nonnenmann, and D. R. Lovley. 2019. The archaellum of *Methanospirillum hungatei* is electrically conductive. mBio. 10:e00579-00519.
37. Walker, D. J. F., K. P. Nevin, S. S. Nonnenmann, D. E. Holmes, T. L. Woodard, J. E. Ward, A.-E. Rotaru, M. J. McInerney, and D. R. Lovley. 2018b. Syntrophus conductive pili demonstrate that common hydrogen-donating syntrophs can have a direct electron transfer option bioRxiv (doi: 10.1038/s41396-019-0575-9).
38. Wals, K. and Ovaa, H. 2014. Unnatural amino acid incorporation in *E. coli*: current and future applications in the design of therapeutic proteins. Front. Chem. 2, 15.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A genetically modified aerobic bacterium, comprising a polynucleotide encoding an electrically conductive fusion protein that comprises a non-native pilin monomer, wherein the non-native pilin monomer comprises an amino acid sequence that has at least 90% sequence identity to the amino acid sequence of wildtype *Geobacter sulfurreducens* PilA monomer (SEQ ID NO:16), wherein the bacterium is an *E. coli* delta type I fimbriae major subunit (ΔfimA), delta flagellin (ΔfliC) cell.

2. The genetically modified aerobic bacterium of claim 1, further comprising a polynucleotide sequence encoding a protein having at least 80% sequence identity to the amino acid sequence of a wildtype pilus assembly protein.

3. The genetically modified aerobic bacterium of claim 2, wherein the pilus assembly protein is an *E. coli* type IV pilus assembly protein.

4. The genetically modified aerobic bacterium of claim 3, wherein the *E. coli* type IV pilus assembly protein is type IV pilus assembly ATPase (hofB), type IV pilus assembly platform protein (hofC), type IV pilus assembly protein M (hofM), type IV pilus assembly protein N (hofN), type IV pilus assembly protein O (hofO), type IV pilus assembly protein P (hovP), type IV pilus assembly secretin (hofQ), minor pilin A (ppdA), minor pilin B (ppdB), minor pilin (ygdB), minor pilin C (ppdC) or prepilin peptidase (gspO), or a combination thereof.

5. The genetically modified aerobic bacterium of claim 4, wherein the bacterium comprises an artificial operon composed of a cluster of two or more polynucleotide sequences encoding pilus assembly proteins.

6. The genetically modified aerobic bacterium of claim 5, wherein the artificial operon is the lac operon.

7. The genetically modified aerobic bacterium of claim 5, wherein the artificial operon comprises hofB-hofC-hofM-hofN-hofO-hovP-hofQ-ppdA-ppdB-ygdB-ppdC-gspO.

8. The genetically modified aerobic bacterium of claim 2, wherein the polynucleotide sequence comprises a ribosome binding site selected from the group consisting of SEQ ID NOs: 1-9 and combinations thereof.

9. The genetically modified aerobic bacterium of claim 5, wherein the polynucleotide sequence comprises a polynucleotide sequence selected from the group consisting of SEQ ID NOs: 10-15 and combinations thereof.

10. The genetically modified aerobic bacterium of claim 2, wherein the polynucleotide sequence is operably linked to an expression control polynucleotide sequence.

11. The genetically modified aerobic bacterium of claim 10, wherein the expression control polynucleotide sequence comprises a strong *E. coli* promoter.

12. The genetically modified aerobic bacterium of claim 11, wherein the strong *E. coli* promoter is the tac promoter.

13. The genetically modified aerobic bacterium of claim 1, wherein the non-native pilin monomer comprises an amino acid sequence that has at least 95% sequence identity to the amino acid sequence of wildtype *Geobacter sulfurreducens* PilA monomer (SEQ ID NO: 16).

14. The genetically modified aerobic bacterium of claim 13, wherein the non-native pilin monomer comprises an amino acid sequence that has at least 98% sequence identity to the amino acid sequence of wildtype *Geobacter sulfurreducens* PilA monomer (SEQ ID NO: 16).

15. A polynucleotide comprising an artificial operon that comprises a cluster of two or more polynucleotide sequences, each polynucleotide sequence encoding a pilus assembly protein.

16. A method of producing electrically conductive protein nanowires, comprising the steps of:

a) placing a genetically modified aerobic bacterium comprising a polynucleotide encoding an electrically conductive fusion protein that comprises a non-native pilin monomer in a culture medium conditioned for producing pili comprising the non-native pilin monomers, wherein the non-native pilin monomer comprises an amino acid sequence that has at least 90% sequence identity to the amino acid sequence of wildtype *Geobacter sulfurreducens* PilA monomer (SEQ ID NO:16), and wherein the bacterium is an *E. coli* delta type I fimbriae major subunit (ΔfimA), delta flagellin (ΔfliC) cell;

b) culturing the bacterium for a time sufficient to produce a desired quantity of the pili; and c) isolating the pili from the culture medium, thereby producing the electrically conductive protein nanowires.

* * * * *